US006555349B1

(12) United States Patent
O'Donnell

(10) Patent No.: US 6,555,349 B1
(45) Date of Patent: Apr. 29, 2003

(54) METHODS FOR AMPLIFYING AND SEQUENCING NUCLEIC ACID MOLECULES USING A THREE COMPONENT POLYMERASE

(75) Inventor: Michael E. O'Donnell, Hastings-on-Hudson, NY (US)

(73) Assignees: Cornell Research Foundation, Inc., Ithaca, NY (US); The Rockefeller University, New York, NY (US)

( * ) Notice: Subject to any disclaimer, the term of this patent is extended or adjusted under 35 U.S.C. 154(b) by 0 days.

(21) Appl. No.: 09/325,067

(22) Filed: Jun. 3, 1999

Related U.S. Application Data

(63) Continuation-in-part of application No. 08/828,323, filed on Mar. 28, 1997, which is a continuation of application No. 08/279,058, filed on Jul. 22, 1994, now Pat. No. 5,668,004, which is a continuation-in-part of application No. 07/826,926, filed on Jan. 22, 1993, now abandoned, application No. 09/325,067, which is a continuation-in-part of application No. 09/282,917, filed on Mar. 31, 1999, now Pat. No. 6,221,642, which is a division of application No. 08/696,651, filed on Aug. 14, 1996, which is a continuation of application No. 08/298,945, filed on Aug. 31, 1994, now Pat. No. 5,583,026.

(51) Int. Cl.[7] .......................... C12Q 1/68; C12P 19/34; C07H 21/02; C07H 21/04
(52) U.S. Cl. .......................... 435/91.2; 435/6; 435/7.1; 435/91.1; 435/194; 530/350; 536/23.1; 536/24.3; 536/24.31; 536/24.32; 536/24.33; 536/22.1
(58) Field of Search .......................... 435/6, 7.1, 91.1, 435/91.2; 530/350, 22.1; 536/23.1, 24.3, 24.31–33

(56) References Cited

U.S. PATENT DOCUMENTS

| 4,394,443 A | 7/1983 | Weissman et al. |
| 5,583,026 A | 12/1996 | O'Donnell |
| 5,668,004 A | 9/1997 | O'Donnell |

FOREIGN PATENT DOCUMENTS

| WO | WO 93/15115 | 8/1993 |
| WO | WO-99/13060 A1 * | 3/1999 |

OTHER PUBLICATIONS

Young et al Biochemistry vol. 21 No. 27 pp. 8675–8690 1992.*

Onrust et al., "DNA Polymerase III Accessory Proteins. II. Characterization of δ and δN," *J. Biol. Chem.* 268:11766–72 (1993).

Dong et al., "DNA Polymerase III Accessory Proteins. I. HolA and holB Encoding δ and δN," *J. Biol. Chem.* 65 268:11758–65 (1993).

Xiao et al., "DNA Polymerase III Accessory Proteins. III. HolC and holD Encoding χ and ψ," *J. Biol. Chem.* 268:11779–84 (1993).

Xiao et al., "DNA Polymerase III Accessory Proteins. IV. Characterization of χ and ψ," *J. Biol. Chem.* 268:11773–78 (1993).

Studwell–Vaughan et al., "DNA Polymerase III Accessory Proteins. V. θ Encoded by holE," *J. Biol. Chem.* 268:11785–91 (1993).

Carter et al., "Molecular Cloning, Sequencing, and Overexpression of the Structural Gene Encoding the δ Subunit of *E. Coli* DNA Polymerase III Holoenzyme," *J. Bacteriol.* 174:7013–25 (1993).

Carter et al., "Identification, Isolation, and Characterization of the Structural Gene Encoding the δN Subunit of *E. Coli* DNA Polymerase III Holoenzyme," *J. Bacteriol,* 175:3812–22 (1993).

Carter et al., "Isolation, Sequencing, and Overexpression of the Gene Encoding the θ Subunit of DNA Polymerase III Holoenzyme," *Nuc. Acids Res.* 21:3281–86 (1993).

Carter et al., "Identification, Isolation, and Overexpression of the Gene Encoding the Ψ Subunit of DNA Polymerase III Holoenzyme," *J. Bacteriol.* 175:5604–10 (1993).

Carter et al., "Identification, Molecular Cloning and Characterization of the Gene Encoding the χ Subunit of DNA Polymerase III Holoenzyme of *E. coli,*" *Mol. Gen. Genet.* 241:399–408 (1993).

Tomasiewicz et al., "Sequence Analysis of the *Escherichia coli* dnaE Gene," *J. Bacteriol.* 169:5735–44 (1987).

Ohmori et al., "Structural Analysis of the dnaA and dnaN Genes of *Escherichia coli,*" *Gene* 28:159–170) (1984).

Flower et al., "The Adjacent dnaZ and dnaX Genes of *Escherichia coli* are Contained Within One Continuous Open Reading Frame," *Nuc. Acids Res,* 14:8091–8101 (1986).

Yin et al., "Nucleotide Sequence of the *Escherichia coli* Replication Gene dnaZX," *ibid.* pp. 6541–6549.

Maki et al., "Structural and Expression of the dnaQ Mutator and the RNase H Genes of *Escherichia coli:* Overlap of the Promoter Regions," *Proc. Natl. Acad. Sci. USA* 80:7137–41 (1983).

Lasken et al., "The βSubunit Dissociates Readily from the *Escherichia coli* DNA Polymerase III Holoenzyme," *J. Biol. Chem.* 262:1720–24 (1987).

Studwell–Vaughan et al., "Constitution of the Twin Polymerase of DNA Polymerase III Holoenzyme," *J. Biol. Chem.* 266(29):19833–41 (1991).

(List continued on next page.)

Primary Examiner—Jeffrey Siew
(74) *Attorney, Agent, or Firm*—Nixon Peabody LLP

(57) ABSTRACT

The present invention is directed to a method for amplifying or sequencing a nucleic acid molecule with a three component polymerase comprising a DNA polymerase component, a sliding clamp component, and a clamp loader component.

42 Claims, 9 Drawing Sheets

OTHER PUBLICATIONS

Maki et al., "DNA Polymerase III Holoenzyme of *Escherichia coli*. IV The Holoenzyme is an Asymmetric Dimer with Twin Active Sites," *J. Biol. Chem,* 263:6570–78 (1988).

Maki et al., "DNA Polymerase III Holoenzyme of *Escherichia coli*. II A Novel Complex Including the γ Subunit Essential for Processive Synthesis," *J. Biol. Chem.* 263(14): 6555–60 (1988).

O'Donnell et al., "Total Reconstitution of DNA Polymerase III Holoenzyme Reveals Dual Accessory Protein Clamps," *J. Biol. Chem.* 265(2):1179–87 (1990).

Blinkova et al., "The *Escherichia coli* DNA Polymerase III Holoenzyme Contains Both Products of the dnaX Gene, τ and γ, but Only τ is Essential," *J. Bacteriol.* 175:6018–27 (1993).

Studwell et al., "Processive Replication is Contingent on the Exonuclease Subunit of DNA Polymerase III Holoenzyme," *J. Biol. Chem.* 265:1171–78 (1990).

Kong et al., "Three–Dimensional Structure of the β Subunit of *E. coli* DNA Polymerase III Holoenzyme: A Sliding DNA Clamp," *Cell* 69:425–37 (1992).

Fradkin et al., "Prereplicative Complexes of Components of DNA Polymerase III Holoenzyme of *Escherichia coli*," *J. Biol. Chem.* 267(15):10318–22 (1992).

Wu et al., "Coordinated Leading– and Lagging–Strand Synthesis at the *Escherichia coli* DNA Replication Fork," *J. Biol. Chem.* 267(6):4064–73 (1992).

Reems et al., "*Escherichia coli* DNA Polymerase III Holoenzyme Footprints Three Helical Turns of Its Primer," *J. Biol. Chem.* 269:33091–96 (1994).

Burgers et al., "ATP Activation of DNA Polymerase III Holoenzyme of *Escherichia coli*," *J. Biol. Chem.* 257(19):11468–73 (1982).

Wu et al., "Coordinated Leading– and Lagging–Strand Synthesis at the *Escherichia coli* DNA Replication Fork," *J. Biol. Chem.* 267(6):4030–44 (1992).

Zechner et al., "Coordinated Leading– and Lagging–Strand Synthesis at the *Escherichia coli* DNA Replication Fork," *J. Biol. Chem.* 267(6):4045–53 (1992).

Zechner et al., "Coordinated Leading– and Lagging–Strand Synthesis at the *Escherichia coli* DNA Replication Fork," *J. Biol. Chem.* 267(6):4054–63 (1992).

Wu et al., "Coordinated Leading– and Lagging–Strand Synthesis at the *Escherichia coli* DNA Replication Fork," *J. Biol. Chem.* 267(6):4074–83 (1992).

Onrust et al., "Analysis of the ATPase Subassembly Which Initiates Processive DNA Synthesis by DNA Polymerase III Holoenzyme," *J. Biol. Chem.* 266(32):21681–86 (1991).

McHenry, "DNA Polymerase III Holoenzyme," *J. Biol. Chem.* 266(29):19127–30 (1991).

Maki et al., "DNA Polymerase III Holoenzyme of *Escherichia coli*," *J. Biol. Chem.* 263(14):6547–54 (1991).

Maki et al., "DNA Polymerase III Holoenzyme of *Escherichia coli*," *J. Biol. Chem.* 263(14):6561–69 (1991).

Maki et al., "The Polymerase Subunit of DNA Polymerase III of *Escherichia coli*," *J. Biol. Chem.* 260(24): 12982–86 (1985).

Maki et al., "The Polymerase Subunit of DNA Polymerase III of *Escherichia coli*," *J. Biol. Chem.* 260(24): 12987–92 (1985).

McHenry, "DNA Polymerase III Holoenzyme of *Escherichia coli*," *Ann. Rev. Biochem.* 57:519–50 (1988).

McHenry et al., "DNA Polymerase III of *Escherichia coli*," *J. Biol. Chem.* 254:1748–53 (1979).

Kornberg, A., "DNA Replication," *W.H. Freeman and Company (San Francisco)* 172–78 (1980).

EMBL database entry #EXCERB, Jul. 6, 1989 (chi DNA sequence).

Ecoseq database entry #YZPA ECOLI, Oct. 1, 1989 (chi peptide sequence).

Stukenberg et al., "Mechanism of the Sliding β–Clamp of DNA Polymerase III Holoenzyme," *J. Biol. Chem.* 266:11328–34 (1991).

EMBL database entry #ECDNAPDPS, Nov. 12, 1992 (delta prime DNA sequence).

EMBL database entry #ECHOLETTA, Nov. 12, 1992 (theta DNA sequence).

Yoshikawa et al., "Cloning and Nucleotide Sequencing of the Genes rimI and rimJ Which Encode Enzymes Acetylating Ribosomal Proteins S18 and S5 of *Escherichia coli* K12,” *Mol. Gen. Genet,* 209:481–88 (1987).

Stirling et al., "xerB, an *Escherichia coli* Gene Required for Plasmid ColE1 Site–Specific Recombination, is Identical to pepA, Encoding Aminopeptidase A, a Protein With Substantial Similarity to Bovine Lens Leucine Aminopeptidase," *EMBO Journal* 8:1623–1627 (1989).

Takase et al., "Genes Encoding Two Lipoproteins in the leuS–dacA Region of the *Escherichia coli* Chromosome," *J. Bact.* 169(12):5692–99 (1987).

Rudinger, "Characteristics of the Amino Acids as Components of a Peptide Hormone Sequence," In: *Peptide Hormones,* J.A. Parsons., Ed., University Park Press, Baltimore, MD., pp. 1–7 (1976).

Ngo et al., "Computational Complexity, Protein Structure Prediction, and the Ilevinthal Paradox," In: *The Protein Folding Problem and Tertiary Structure Prediction,* Merz et al., Eds., Brikhauser et al., Boston, MA., pp. 491–495 (1994).

Thornton et al., "Protein Engineering: Editorial Overview," *Current Opinion in Biotechnology* 6:367–369 (1995).

Wallace, "Understanding Cytochrome C Function: Engineering Protein Structure by Semisynthesis," *The FASEB Journal* 7:505–515 (1993).

O'Donnell et al., "Homology in Accessory Proteins of Replicative Polymerases—*E. coli* to Humans," *Nucleic Acids Research* 21:1–3 (1993).

Sanders et al., "Rules Governing the Efficiency and Polarity of Loading a Tracking Clamp Protein Onto DNA: Determinants of Enhancement in Bacteriophage T4 Late Transcription," *The EMBO Journal* 14:3966–3976 (1995).

Stillman, "Smart Machines at the DNA Replication Fork," *Cell* 78:725–728 (1994).

Krishna et al., "Crystal Structure of the Eukaryotic DNA Polymerase Processivity Factor PCNA," *Cell* 79:1233–1243 (1994).

Kelman et al., "Structural and Functional Similarities of Prokaryotic and Eukaryotic DNA Polymerase Sliding Clamps," *Nucleic Acids Research* 23:3613–3620 (1995).

Tsurimoto et al., "Functions of Replication Factor C amd Proliferating–Cell Nuclear Antigen: Functional Similarity of DNA Polymerase Accessory Proteins From Human Cells and Bacteriophage T4," *Proc. Natl. Acad. Sci. USA,* 87:1023–1027 (1990).

Cullmann et al., "Characterization of the Five Replication Factor C Genes of *Saccharomyces Cerevisiae*," *Molecular and Cellular Biology* 15:4661–4671 (1995).

* cited by examiner

METHODS FOR AMPLIFYING AND SEQUENCING NUCLEIC ACID MOLECULES USING A THREE COMPONENT POLYMERASE

The present application is a continuation-in-part of U.S. patent application Ser. No. 08/828,323, filed Mar. 28, 1997, which is a continuation of Ser. No. 08/279,058, filed Jul. 22, 1994, now issued as U.S. Pat. No. 5,668,004, which is a continuation-in-part of U.S. patent application Ser. No. 07/826,926, filed Jan. 22, 1993, now abandoned. The present application is also a continuation-in-part of U.S. patent application Ser. No. 09/282,917, filed Mar. 31, 1999, now issued as U.S. Pat. No. 6,221,642, which a division of U.S. patent application Ser. No. 08/696,651, filed Aug. 14, 1996, which is a continuation of U.S. patent application Ser. No. 08/298,945, filed Aug. 31, 1994, now issued as U.S. Pat. No. 5,583,026.

This invention was made based on funding under National Institutes of Health Grant No. GM38839. The United States Government may have certain rights.

FIELD OF THE INVENTION

The present invention relates to the use of cellular chromosomal replicases of the three-component type in bioinformatic techniques such as the sequencing and amplification of DNA. The three components of these DNA polymerases are 1) a catalytic component with polymerase activity, 2) a circular protein that functions as a sliding clamp to tether the polymerase component to DNA for processivity, and 3) a clamp loader that assembles the sliding clamp onto DNA for high processivity. The clamp endows the polymerase with enhanced catalytic efficiency.

BACKGROUND OF THE INVENTION

DNA Sequencing

In general, two techniques have been traditionally used to sequence nucleic acids:

The Sanger technique, also known as the dideoxy sequencing method, is used for determining the unknown nucleotide sequence of a particular nucleic acid. The DNA to be analyzed must first be isolated into a single-stranded form in order to serve as a template for the synthesis of complementary DNA. The template is hybridized to a primer and then incubated with a mixture of the four deoxyribonucleoside triphosphates and small amounts of a single chain-terminating 2',3'-dideoxynucleoside triphosphate (lack a 3'-OH group) in the presence of the enzyme DNA polymerase. DNA polymerase is used, because it has the ability to synthesize a complementary copy of a single-stranded DNA template and it can also use 2',3'-dideoxynucleoside triphosphate as a substrate.

The analogs become incorporated at the growing ends of the DNA chains resulting in chain termination since they cannot form phosphodiester bonds with incoming precursors. Thus, in the absence of the hydroxyl group, the DNA fragment is no longer a substrate for chain elongation and the growing DNA chain is terminated. The DNA synthesis is carried out in the presence of the four deoxyribonucleoside triphosphates, one or more of which is labeled with $^{32}$P, in four reaction mixtures each of which contains one of the dideoxy compounds. Upon completion of each reaction, the final reaction mixture will contain a series of fragments of new DNA, each having a common 5'-end but varying in length to a base-specific 3'-end. Following synthesis, the reaction products are separated from the template by denaturation and separated by electrophoresis. The positions of the fragments on the gel are visualized by autoradiography and the DNA sequence read directly from the autoradiogram.

The Maxam-Gilbert sequencing method uses chemical reagents that react with specific bases to break DNA preferentially at specific sites. First, the strands of the target DNA molecule are labeled with $^{32}$P at one end and the two strands are separated so that one can be sequenced. Next, the single-stranded DNA strand to be sequenced will be treated with four different chemical reagents that specifically react with one of the four bases causing a break in the strand at one or two specific nucleotides. A specific amount of chemical treatment is used so that at most a single residue of the susceptible bases(s) in the molecule will react. The reaction will yield a product labeled at the 5' end with $^{32}$P and terminating at the point of cleavage.

Gel electrophoresis is used to resolve the products of each reaction by size. The pattern of radioactive bands seen on the X-ray reveals the DNA sequence. By correlating the appearance of fragments of specified length with the specific base destroyed by chemical attack, the exact order of bases along the original unbroken DNA strand can be determined.

The Polymerase Chain Reaction

A targeted DNA sequence can be selectively and repeatedly amplified in vitro by use of the PCR method. An advantage of this method is that it requires only a small quantity of the DNA that is to be amplified. Restriction enzymes are used to cut the DNA into segments, and the segments are denatured into single strands. Two flanking oligonucleotide primers complementary to the 3' ends of the DNA are required at the ends of the DNA segment to be amplified. The probe is added in significant excess to the denatured DNA at a temperature between 50° C. and 60° C. The probe hybridizes with its correct site on the DNA and serves as a primer for DNA chain synthesis, which begins upon addition of a supply of deoxynucleotides and the temperature resistant Taq DNA polymerase. After annealing, the primers 3' ends face each other as a result of having complementary opposite strands.

The three steps involved in a PCR reaction are: 1) denaturation of the original double-stranded DNA sample at a high temperature; 2) annealing of the oligonucleotide primers to the DNA template at low temperature (e.g., about 37° C.); and 3) extension of the primers using DNA polymerase. The DNA polymerase that is currently used is Taq DNA polymerase which is thermostable and unaffected by the denaturation temperature. Each set of three steps is a cycle which is repeated many times in a PCR process. The extension products of one primer provide a template for the other primer in a subsequent cycle so that each successive cycle essentially doubles the amount of DNA synthesized in the previous cycle. The result is an exponential accumulation of the specific target fragment to approximately $2^n$, where n is the number of cycles.

The present invention is directed to improved processes of sequencing and amplifying DNA.

SUMMARY OF THE INVENTION

The present invention relates to a method for amplifying a nucleic acid molecule comprising subjecting the nucleic acid molecule to a polymerase chain reaction process utilizing a three component polymerase.

Another aspect of the present invention relates to a method for sequencing a nucleic acid molecule which includes subjecting the nucleic acid molecule to a nucleic acid sequencing process with a three component polymerase.

The invention further provides kits for amplifying and sequencing a DNA molecule.

The methods and kits of the present invention, utilizing compositions comprising a three component polymerase, such as DNA polymerase III ("Pol III") type enzyme from a single cell organism, provide a number of advantages over traditional PCR-based methods using other polymerases. In particular, the three component polymerase of the present invention permits a reduction in time required for nucleic acid amplification and sequencing. Because DNA Pol III-type enzymes have a faster rate of nucleotide incorporation than the repair-type enzymes commonly used in these techniques, for a 1–5 kb sequence, the protocol for amplification or sequencing can be reduced from several hours (or 10–20 hours in the case of long PCR on nucleic acid molecules 5–40 kb in size) to less than one hour, resulting in a reduction in thermal damage to the template nucleic acid molecule. Because the amplification and sequencing reactions utilizing DNA Pol III-type enzymes proceed more rapidly, the template is exposed to high temperatures for shorter periods of time. This reduction of thermal damage is particularly important in long PCR, where the ultimate success of the procedure is dependent upon a minimization of thermal damage to the target nucleic acid molecule, particularly during later cycles. The present invention should improve yields for sequences up to 50 kb in length, and, for the first time, enable the amplification of sequences of 100 kb or larger. In addition, the relatively long times required for traditional PCR-based amplification and sequencing protocols using repair-type enzymes tends to promote the formation of short, nonspecific reaction products (e.g., truncated copies of the template molecule). Rapid extension of the correct template sequence, afforded by the present invention, will reduce the number of false priming interactions that occur and, thus, provide an improvement in the specificity of the reaction. The ability of DNA Pol III-type enzymes to synthesize long sequences without dissociating from the template nucleic acid molecule, via the methods of the present invention, will improve success in long PCR by allowing nucleic acid synthesis through secondary structures and regions of high GC content in the template which tend to retard or inhibit synthesis in reactions catalyzed by the repair-type enzymes.

DETAILED DESCRIPTION OF THE INVENTION

Figure 1:
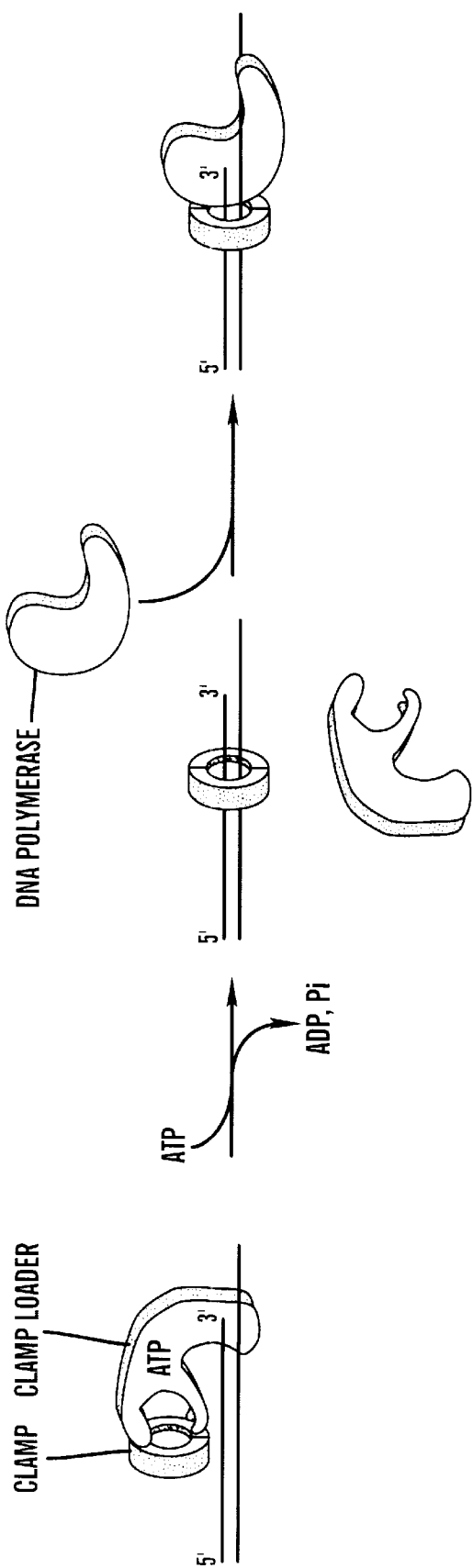
FIG. 1 shows the operation of a three component polymerase in which the clamp loader loads a circular sliding clamp protein onto DNA (step 1) followed by interaction of the polymerase component with the clamp loader (step 2).

In all cellular systems studied thus far, the chromosomal DNA polymerase is composed of three basic components: 1) the DNA polymerase, 2) a sliding clamp, and 3) a clamp loader (see FIG. 1). The sliding clamp is an oligomer of identical subunits that forms a ring for encircling DNA. This ring of protein slides freely along duplex DNA and it functions as a mobile tether to hold the DNA polymerase to DNA for efficient processive DNA synthesis. The clamp of the prokaryotic three component polymerase Pol III type enzyme is called $\beta$ (homodimer), the clamp of the eukaryotic three component polymerase is PCNA (homotrimer), the clamp of the archaebacterial three component polymerase is also a PCNA homotrimer. The clamp requires another component, the clamp loader, for assembly onto DNA in a reaction that generally requires ATP. The clamp loader is composed of more than one subunit in all organisms. The bacterial clamp loader is referred to as the $\gamma$ complex, while the eukaryotic clamp loader is referred to as RFC although its subunits show homology to prokaryotic γ subunit (O'Donnell et al., "Homology in Accessory Proteins of Replicative Polymerases-*E. coli* to Humans," *Nucleic Acids Res.*, 21:1–3 (1993); Cullman et al., "Characterization of the Five Replication Factor C Genes of *Saccharomyces cerevisiae*," *Mol. Cell Biol.*, 15:4661–4671 (1995), which are hereby incorporated by reference), thermophilic bacteria (Deckert et al., "The Complete Genome of the Hyperthermophilic Bacterium *Aquifex aeolicus*," *Nature*, 392:353–358 (1998), which is hereby incorporated by reference), and the archaebacterial clamp loader is also referred to as RFC and its subunits share homology with γ as well (Bult et al., "Complete Genome Sequence of the Methanogenic Archaeon, *Methanococcus jannaschii*," *Science*, 273:1058–1073 (1996); Klenk et al., "The Complete Genome Sequence of the Hyperthermophilic, Sulphate-Reducing Archaeon *Archaeoglobus fulgidus*," *Nature*, 390:364–370 (1997), which are hereby incorporated by reference). These clamp and clamp loader components are sometimes referred to as accessory proteins, or processivity factors, as they provide processivity to DNA polymerases. In each cell type they may provide processivity to more than one DNA polymerase. For example, in eukaryotes, PCNA/RFC provides processivity to at least two polymerases examined thus far, DNA polymerase δ and DNA polymerase ε. Bambara et al., "Properties of DNA Polymerases δ and ε, and Their Roles in Eukaryotic DNA Replication," *Biochemica et. Biophysica Acta* 1088:11–24 (1991), which is hereby incorporated by reference. In prokaryotes, the β/γ complex provides processivity to DNA polymerase II and to the replicative polymerase, DNA polymerase III (Bonner et al., "Processive DNA Synthesis by DNA Polymerase II Mediated by DNA Polymerase III Accessory Proteins," *J. Biol. Chem.* 267(16):11431–11438 (1992); Hughes, A. J., et al. "*Escherichia coli* DNA Polymerase II is Stimulated by DNA Polymerase III Holoenzyme Auxiliary Subunits," *J. Biol. Chem.* 266(7):4568–4573 (1991), which are hereby incorporated by reference).

During the process of chromosome replication, these three component DNA polymerases function with yet other enzymes. The two strands of duplex DNA must be unwound into two single strands which can then serve as templates for conversion into two new duplex DNA molecules by the three-component polymerase. This DNA unwinding is performed by a helicase which uses ATP to separate the DNA strands. In prokaryotes, such as *E. coli*, the helicase (DnaB protein) is contacted directly via τ, one of the subunits of the three-component DNA polymerase (Pol III). This contact speeds the helicase to match the approximate 1 kb/s speed of the three-component DNA polymerase (Kim et al., "Coupling of a Replicative Polymerase and Helicase: a tau-DnaB Inter-action Mediates Rapid Replication Fork Movement," *Cell*, 84:643–650 (1996); Yuzhakov et al., "Replisome Assembly Reveals the Basis for Asymmetric Function in Leading and Lagging Strand Replication," *Cell*, 86:877–886 (1996), which are hereby incorporated by reference), and it helps hold the polymerase to DNA during the long synthetic process.

The three-component polymerases are thought to dimerize in order to synthesize both unwound strands simultaneously and thereby achieve coordination during the synthesis of the two strands. In *E. coli*, a prokaryote, two Pol III polymerases are connected by τ, the same protein that binds the DnaB helicase (Onrust et al., "Assembly of a Chromosomal Replication Machine: Two DNA Polymerases, a Clamp Loader, and Sliding Clamps in One Holoenzyme Particle. III. Interface Between Two Polymerases and the Clamp Loader," *J. Biol. Chem.*, 270:133366–13377 (1995), which is hereby incorporated by reference). In yeast, a eukaryote, the DNA polymerase δ becomes dimerized via self interaction between one of its subunits (Burgers et al., "Structure and Processivity of Two Forms of *Saccharomyces cerevisiae* DNA Polymerase δ*," *J. Biol. Chem.*, 273:19756–19762 (1998).

The processive polymerase/clamp on one strand synthesizes DNA in the same direction as helicase catalyzed unwinding (i.e., with the replication fork). This strand is called the leading strand. However, due to the antiparallel orientation of the two DNA strands in the duplex, the other strand is replicated in the direction opposite helicase movement. This strand is called the lagging strand. Hence, this lagging strand is made discontinuously as a series of fragments, and the polymerase must repeatedly hop from the end of a finished fragment, to a new position back near the fork for the next fragment. As these DNA polymerases cannot initiate DNA synthesis de novo, another enzyme is required to make a primed start for each new lagging strand fragment. This enzyme, called primase, makes a short RNA primer for use by the three-component polymerase. In prokaryotes, this primase is the DnaG protein, and, in eukaryotes, it is DNA polymerase α/primase (Marians, K. J, "Prokaryotic DNA Replication,"*Annu Rev. Biochem.*, 61:673–7198 (1992); Waga et al., "The DNA Replication Fork in Eukaryotic Cells," *Annu. Rev. Biochem.*, 67:721–751 (1998), which are hereby incorporated by reference).

On single strand DNA (ssDNA), these three-component polymerases require a protein called ssDNA binding protein ("SSB") for efficient DNA chain elongation. SSB binds ssDNA and removes secondary structure, such as hairpins, which would ordinarily impede DNA polymerase progression. In prokaryotes, this protein is called SSB, and, in eukaryotes, it is referred to as RPA (Marians, K. J, "Prokaryotic DNA Replication," *Annu Rev. Biochem.*, 61:673–7198 (1992); Waga et al., "The DNA Replication Fork in Eukaryotic Cells," *Annu. Rev. Biochem.*, 67:721–751 (1998), which are hereby incorporated by reference).

These three-component polymerases thus have several features that distinguish them from the polymerases that are currently used in sequencing and amplification. The Pol I, T4 Pol, and Taq polymerases are much less processive and are slower. At 37° C., Pol I proceeds at 10–20 nucleotides per second with a processivity of about 10–50 nucleotides, while Pol III/β/γ complex extends DNA at 500–800 nucleotides each second at 30° C. to 37° C. with a processivity of over 50 kb and, perhaps, as much as 4.6 Mb, the length of the *E. coli* chromosome (Mok et al., "The *Escherichia coli* Preprimosome and DnaB Helicase Can Form Replication Forks that Move at the Same Rate," *J. Biol. Chem.*, 262:16558–16565 (1987); O'Donnell et al, "Dynamics of DNA Polymerase III Holoenzyme of *Escherichia coli* in Replication of a Multiprimed Template," *J. Biol. Chem.*, 260:12875–12883 (1985); Burgers et al., "ATP Activation of DNA Polymerase III Holoenzyme from *Escherichia coli*. II. Initiation Complex: Stoichiometry and Reactivity," *J. Biol. Chem.*, 257:11474–11478 (1982), which are hereby incorporated by reference). Although Taq polymerase achieves speeds of 100 nucleotides per second or more at high temperature, it is not a highly processive enzyme and it lacks inherent capacity to proofread its DNA product. By contrast, three component enzymes probably all have inherent 3'-5' proofreading exonuclease activity, as described below for the specific case of *E. coli*. T7 based sequenase is processive but is not as fast as the *E. coli* three component polymerase. Further, the three-component polymerases operate with a helicase (Kim et al., "Coupling of a Replicative Polymerase and Helicase: a tau-DnaB Inter-action Mediates Rapid Replication Fork Movement," *Cell*, 84:643–650 (1996); Yuzhakov et al., "Replisome Assembly Reveals the Basis for Asymmetric Function in Leading and Lagging Strand Replication," *Cell*, 86:877–886 (1996), which are hereby incorporated by reference) which, in some applications, could provide the ability to melt DNA and thereby amplify it without thermal DNA denaturation.

The present invention relates generally to using small three-component DNA polymerases for nucleic acid sequencing and amplification. One example of a three-component DNA polymerase is the *E. coli* three-component polymerase which is described below.

DNA polymerase III ("Pol III") was first purified and determined to be the principal replicase of the *E. coli* chromosome by Kornberg (Kornberg, A., 1982 *Supplement to DNA Replication,* Freeman Publications, San Francisco, pp 122–125), which is hereby incorporated by reference. The three components of the *E. coli* DNA Polymerase III can be assembled into one holoenzyme where they are all connected together. This holoenzyme comprised of 10 subunits (McHenry, et al., *J. Bio Chem.*, 252:6478–6484 (1977) and Maki, et al., *J. Biol. Chem.*, 263:6551–6559 (1988), which are hereby incorporated by reference) and these subunits are set forth in Table 1 as follows.

TABLE 1

| Gene | Subunit | Mass (kda) | Functions | | |
|---|---|---|---|---|---|
| dnaE | α | 130 | DNA Polymerase | Core Pol III | |
| dnaQ | ε | 27 | Proofreading 3'-5' exonuclease | | |
| hol E | θ | 10 | Binds ε | | |
| dnaX | τ | 71 | Dimerizes core, Binds to DnaB helicase | Pol III | |
| dnaX | γ | 47 | Clamp loader motor | | Pol III* |
| holA | δ | 35 | Clamp opener | γ complex | |
| holB | δ' | 33 | Modulator of δ | | |
| holC | χ | 15 | Primase-Polymerase switch | | |
| holD | ψ | 12 | Joins χ to γ | | |
| dnaN | β | 40 | Sliding clamp on DNA, binds core | clamp | |

The three components of Pol III are: the core (i.e. the polymerase), β (i.e. the clamp), and the γ complex (i.e. clamp loader). The τ subunit holds together two cores to form the Pol III' subassembly, and it binds one γ complex to form Pol III*. The τ subunit and the γ subunit are both encoded by dnaX. τ is the full length product. γ is approximately the N terminal ⅔ of τ and is formed by a translational frame shift (Tsuchihashi et al., "Translational Frameshifting Generates the γ Subunit of DNA Polymerase III Holoenzyme," *Proc. Natl. Acad. Sci., USA*, 87:2516–2520 (1990), which is hereby incorporated by reference). Within the core are three subunits as follows: the α subunit (dnaE) contains the DNA polymerase activity (Blanar, et al., *Proc. Natl Acad. Sci. USA*, 81:4622–4626 (1984), which is hereby incorporated by reference); the ε subunit (dnaQ, mutD) is the proofreading 3'-5' exonuclease (Scheuermann, et al., *Proc. Natl. Acad. Sci. USA*, 81:7747–7751 (1985) and DeFrancesco, et al., *J. Biol. Chem.*, 259:5567–5573 (1984), which are hereby incorporated by reference), and the θ subunit (holE) stimulates ε (Studwell-Vaughan et al., "DNA Polymerase III Accessory Proteins V. θ encoded by holE*," *J. Biol. Chem.*, 268:11785–11791 (1993), which is hereby incorporated by reference). The α subunit forms a tight 1:1 complex with ε (Maki, et al., *J. Biol. Chem.*, 260:12987–12992 (1985) which is hereby incorporated by reference, and θ forms a 1:1 complex with ε (Studwell-Vaughan et al., "DNA Polymerase III Accessory Proteins V. θ encoded by holE*," *J. Biol. Chem.*, 268:11785–11791 (1993), which is hereby incorporated by reference).

The γ complex clamp loader consists of 5 subunits (i.e. γδδ'χΨ) (Kelman et al., "DNA Polymerase III Holoenzyme: Structure and Function of a Chromosomal Replicating Machine," *Ann. Rev. Biochem.*, 64:171–200 (1995), which is hereby incorporated by reference). The γ subunit is the motor and is the only subunit that interacts with ATP. The δ subunit (holA) is the clamp opener as it binds the circular β homodimer and opens it at one interface. The δ' subunit (holB), shaped like a C, modulates access of β to δ via ATP coupled conformation changes in γ. The χ subunit (holC) binds SSB and functions to displace primase from an RNA primed site. The Ψ subunit (hol D) bridges the contact between γ and χ.

The β sliding clamp (i.e. dnaN) is a tight head-to-tail homodimer shaped as a ring; each protomer is comprised of 3 domains of identical chain folding topology giving the ring a 6-fold appearance (Krishna et al., "Crystal Structure of the Eukaryotic DNA Polymerase Processivity Factor PCNA," *Cell*, 79:1233–1243 (1994), which is hereby incorporated by reference). The ring binds to the polymerase core component thereby holding it to DNA for high processivity (Stukenberg et al., "Mechanism of the Sliding U-clamp of DNA Polymerase III Holoenzyme," *J. Biol. Chem.*, 266:11328–11334 (1991), which is hereby incorporated by reference).

The universal similarity of cellular chromosome replication by 3-component replicases is exemplified by comparing the *E. coli* and human replicases. The PCNA clamp is a six domain ring with inner and outer diameters similar to the β ring and the same chain fold as the domains of PCNA and β (Gulbis et al., "Structure of the C-Terminal Region of p21$^{WAF1/C1P1}$ Complexed With Human PCNA," *Cell* 87:297–306 (1996); Kong et al., "Three-Dimensional Structure of the β Subunit of *E. coli* DNA Polymerase III Holoenzyme: A Sliding DNA Clamp," *Cell* 69:425–437 (1992); and Krishna et al., "Crystal Structure of the Eukaryotic DNA Polymerase Processivity Factor PCNA," *Cell* 79:1233–1243 (1994), which are hereby incorporated by reference). The only obvious difference between PCNA and β is that each monomer is composed of only two domains and, thus, trimerizes to form a six domain ring. The human RF-C clamp loader contains 5 proteins, like the γ complex, and its subunits show homology to the γ and δ' subunits of the γ complex (O'Donnell et al., "Homology in Accessory Proteins of Replicative Polymerases-*E. coli* to Humans," *Nucleic Acids Res.*, 21:1–3 (1993); Cullman et al., "Characterization of the Five Replication Factor C Genes of *Saccharomyces cerevisiae,*" Mol. Cell Biol., 15:4661–4671 (1995), which are hereby incorporated by reference). The DNA polymerase δ, like the core, is composed of several subunits and contains both polymerase and 3'-5' exonuclease activities (Waga et al., "The DNA Replication Fork in Eukaryotic Cells," *Annu. Rev. Biochem.*, 67:721–751 (1998); Burgers et al.,"Structure and Processivity of Two Forms of *Saccharomyces cerevisiae* DNA Polymerase δ*,"

*J. Biol. Chem.*, 273:19756–19762 (1998) and Zuo et al., "DNA Polymerase δ Isolated from *Schizosaccharomyces pombe* Contains Five Subunits," *Proc. Natl. Acad. Sci USA.*, 94:11244–11249 (1997), which are hereby incorporated by reference).

The *E coli* three-component polymerase is highly efficient and completely replicates a uniquely primed bacteriophage single-strand DNA ("ssDNA") genome coated with the ssDNA binding protein ("SSB"), at a speed of at least 500 nucleotides per second at 30° C. without dissociating from a 5 kb circular DNA even once (Fay, et al., *J. Biol. Chem.*, 256:976–983 (1981); O'Donnell, et al., *J. Biol. Chem.*, 260:12884–12889 (1985); and Mok, et al., *J. Biol. Chem.*, 262:16644–16654 (1987), which are hereby incorporated by reference). This remarkable processivity (i.e., the high number of nucleotides polymerized in one template binding event) and catalytic speed is in keeping with the rate of replication fork movement in *E. coli* (i.e. about 1 kb/second at 37° C.) (Chandler, et al.,*J. Mol. Biol.*, 94:127–131 (1975), which is hereby incorporated by reference).

DNA polymerase I, as well as the T4 DNA polymerase, T7 sequenase, and Taq DNA polymerases, are all 3–10 fold slower and less processive than three-component polymerase. Thus, due to the speed and high processivity of three-component polymerases, they have commercial application. Previously, there was a good reason these three component polymerases have not yet been applied commercially. Namely, they are composed of multiple subunits and are present in small amounts inside cells making them difficult to purify. The multicomponent structure prevents them from being simply overproduced by genetic engineering. However, recent techniques have allowed for the production of the *E. coli* three-component polymerase by reconstitution (see U.S. Pat. No. 5,583,026 to O'Donnell, which is hereby incorporated by reference) and recombinant techniques (see U.S. Pat. No. 5,668,004 to O'Donnell, which is hereby incorporated by reference). This provides precedent and encouragement for producing large amounts of three-component polymerases from other sources, such as other bacteria, eukaryotes, thermostable bacteria, and archaebacteria. The efficiency of three-component polymerases and their use from thermophilic sources makes them attractive reagents for use in sequencing and amplification techniques. Further, their ability to function with helicases (See e.g., Yuzhakov et al., "Replisome Assembly Reveals the Basis for Asymmetric Function in Leading and Lagging Strand Replication," *Cell*, 86:877–886 (1996) and Mok et al., "The *Escherichia coli* Preprimosome and DnaB Helicase Can Form Replication Forks that Move at the Same Rate," *J. Biol. Chem.*, 262:16558–16565 (1987), which are hereby incorporated by reference), enable isothermal polymerase chain reaction. Thus, the present invention is directed toward capitalizing on these special features, including speed and processivity of the three component class of polymerases.

The three component polymerase for use in the present invention may be isolated from any organism that makes a three component polymerase naturally, or it may be produced recombinantly. The three component polymerase complexes may be thermolabile (i.e. isolated from a variety of mesophilic or chrysophilic organisms), or they may be thermostabile (i.e. isolated from a variety of thermophilic organisms).

As used herein "thermostable" refers to a DNA polymerase which is resistant to inactivation by heat. DNA polymerases synthesize the formation of a DNA molecule complementary to a single-stranded DNA template by extending a primer in the 5'-to-3' direction. As used herein, a thermostable DNA polymerase is more resistant to heat inactivation than a thermolabile DNA polymerase (defined below). However, a thermostable DNA polymerase is not necessarily totally resistant to heat inactivation, and, thus, heat treatment may reduce the DNA polymerase activity to some extent. A thermostable DNA polymerase typically will also have a higher optimum temperature for synthetic function than thermolabile DNA polymerases. Thermostable DNA polymerases are typically isolated from thermophilic organisms, for example, thermophilic bacteria.

Thermostable three component polymerase complexes may be isolated from a variety of thermophilic bacteria that are available commercially (for example, from American Type Culture Collection, Rockville, Md.). Suitable for use as sources of thermostable enzymes are the thermophilic bacteria *Thermus aquaticus, Thermus thermophilus, Thermococcus litoralis, Pyrococcusfuriosus, Pyrococcus woosii,* other species of the Pyrococcus genus, *Bacillus stearothermophilus, Sulfolobus acidocaldarius, Thermoplasma acidophilum, Thermusflavus, Thermus ruber, Thermus brockianus, Thermotoga neaPolitana, Thermotoga maritima,* other species of the Thermotoga genus, *Methanobacterium thermoautotrophicum,* and mutants of each of these species. It will be understood by one of ordinary skill in the art, however, that any thermophilic microorganism might be used as a source of thermostable three component polymerase. Bacterial cells may be grown according to standard microbiological techniques, using culture media and incubation conditions suitable for growing active cultures of the particular thermophilic species that are well-known to one of ordinary skill in the art (see, e.g., Brock, T. D., and Freeze, H., *J. Bacteriol.*, 98(1):289–297 (1969); Oshima, T., and Imahori, K, *Int. J. Syst. Bacteriol.*, 24(l):102–112 (1974), which are hereby incorporated by reference).

As used herein "thermolabile" refers to a DNA polymerase which is not resistant to inactivation by heat. For example, T5 DNA polymerase, the activity of which is totally inactivated by exposing the enzyme to a temperature of 90° C. for 30 seconds, is considered to be a thermolabile DNA polymerase. As used herein, a thermolabile DNA polymerase is less resistant to heat inactivation than is a thermostable DNA polymerase. A thermolabile DNA polymerase typically is also likely to have a lower optimum temperature than a thermostable DNA polymerase. Thermolabile DNA polymerases are typically isolated from mesophilic organisms, for example, mesophilic bacteria or eukaryotes, including certain animals.

Such mesophilic organisms include mesophilic bacterial cells, mesophilic yeast cells, mesophilic animal cells, and mesophilic plant cells. Preferred mesophilic bacterial cells include, but are not limited to, *Escherichia coli* cells, Bacillus spp. cells, Salmonella spp. cells, Streptococcus spp. cells, and Staphylococcus spp. cells, and, particularly preferred, *Escherichia coli* cells. Preferred mesophilic yeast cells include, but are not limited to, *Saccharomyces* spp. cells. Preferred mesophilic animal cells include, but are not limited to, insect cells, preferably cells isolated from Drosophila, Spodoptera, or Trichoplusa species, nematode cells, preferably isolated from *C. elegans,* and mammalian cells, preferably isolated from humans. Such mesophilic cells may be isolated according to art-known methods or may be obtained commercially, for example from American Type Culture Collection, Rockville, Md., and may be cultured according to standard culture methodologies that are well-known to one of ordinary skill in the art. Methods for isolating thermolabile three component polymerases from such cells are described in McHenry et al., "DNA Polymerase III Holoenzyme of *Escherichia coli,*" *J. Biol. Chem.* 252(18):6478–6484 (1977); Cull et al., "Purification of *Escherichia coli* DNA Polymerase III Holoenzyme," *Methods in Enzymology* 262:22-et. seq. (1995); and Maki, S., and Kornberg, A., *J. Biol. Chem.* 263:6555–6560 (1988), which are hereby incorporated by reference.

Especially preferred is the *E. coli* DNA Pol III described in U.S. Pat. Nos. 5,583,026 and 5,668,004 to O'Donnell, which are hereby incorporated by reference.

As used herein, the term three component polymerase refers to the three components of a replicative polymerase which, when operative on DNA, consists of a sliding clamp that confers enhanced synthetic capability onto a DNA polymerase. The clamp loader may or may not be attached to the polymerase via intrasubunit contacts. The term "Pol III-type" polymerase is synonymous with the term "three component polymerase".

As used herein, "enzyme complex" refers to a multi-protein structure such as a clamp loader, a multi-subunit polymerase, or a complex including the clamp loader, the polymerase, and the clamp, or multi-protein subassemblies of these components or combinations of two or three of these components or their subassemblies. An enzyme complex according to this definition ideally will have a particular enzymatic activity, which may be different from or up to and including, the activity of all the components mixed together.

Preferably, the enzyme complex is substantially reduced in 3'-5' exonuclease activity, especially when high amounts of the enzyme are present in the reaction. "Substantially reduced in 3'-5' exonuclease activity" (which may also be represented as "exo-") is defined herein as (1) a DNA polymerase component or three component polymerase that is lacking one or more subunits of the native or wild-type component complex such that the polymerase has about or less than 10%, or preferably about or less than 1%, of the 3'-5' exonuclease activity of the corresponding native or wild-type polymerase; (2) a mutated DNA polymerase or polymerase subunit (e.g., ε) that has about or less than 10%, or preferably about or less than 1%, of the 3'-5' exonuclease activity of the corresponding nonmutated, wild-type enzyme; or (3) a DNA polymerase having 3'-5' exonuclease specific activity which is less than about 1 unit/mg protein, or preferably about or less than 0.1 units/mg protein. As disclosed in Scheuermann, et al., *Proc. Natl. Acad. Sci. USA,* 81:7747–7751 (1985) and DeFrancesco, et al., *J. Biol. Chem.,* 259:5567–5573 (1984), which are hereby incorporated by reference, the ε subunit of the *E. coli* Pol III contains the 3'-5' exonuclease activity. Accordingly, preferably, the polymerase component of the present invention does not include the ε subunit. In addition, preferably, the polymerase component does not include the θ subunit since θ needs ε to assemble into the complex. An enzyme complex in which τ is substituted for γ in the clamp loader and is associated with the polymerase component via τ is also preferred.

The *E. coli* Pol III has traditionally been difficult to obtain in large quantity, because of its low cellular concentration (O'Donnell, *Bioassays,* 14:105–111 (1992), which is hereby incorporated by reference). However, all ten subunits comprising Pol III are now available in abundance by molecular cloning of their genes and high level expression techniques (Onrust, R., et al., "DNA Polymerase III Accessory Proteins. II. Characterization of δ and δ'," *J. Biol. Chem.,* 268:11766–11772 (1993); Dong, A., et al., "DNA Polymerase III Accessory Proteins. I. ho1A and ho1B Encoding δ and δ'," *J. Biol. Chem.,* 268:11758–11765 (1993); Xiao, H., et al., "DNA Polymerase III Accessory Proteins. III. ho1C and ho1D Encoding χ and Ψ," *J. Bio. Chem.,* 268:11773–11778 (1993); Xiao, H., et al., "DNA Polymerase III Accessory Proteins. IV. Characterization of χ and Ψ," *J. Bio. Chem.,* 268:11773–11778 (1993); Studwell-Vaughan, P. S., et al., "DNA Polymerase III Accessory Proteins. V. θ Encoded by holE," *J. Biol. Chem.,* 268:11785–11791 (1993); Carter, J. R., et al., "Molecular Cloning, Sequencing, and Overexpression of the Structural Gene Encoding the δ Subunit of *E. coli* DNA Polymerase III Holoenzyme," *J. Bacterial.,* 174:7013–7025 (1993); Carter, J. R., et al., "Identification, Isolation, and Characterization of the Structural Gene Encoding the δ Subunit of *E. coli* DNA Polymerase III Holoenzyme," *J. Bacteriol,* 175:3812–3822 (1993); Carter, J. R., et al., "Isolation, Sequencing and Overexpression of the Gene Encoding the θ Subunit of DNA Polymerase III Holoenzyme," *Nuc. Acids Res.,* 21:3281–3286 (1993); Carter, J. R., et al., "Identification, Isolation, and Overexpression of the Gene Encoding the Ψ Subunit of DNA Polymerase III Holoenzyme," *J. Bacteriol,* 175:5604–5610 (1993); and Carter, J. R., et al., "Identification, Molecular Cloning and Characterization of the Gene Encoding the χ Subunit of DNA polymerase III Holoenzyme of *E. coli,*" Mol. Gen. Genet., 241:399–408 (1993), which are hereby incorporated by reference). The gene sequences for these subunits are also disclosed in O'Donnell, International Application No. WO93/15115, filed Jan. 24, 1993; Tomasiewicz, et al., *J. Bacteriol,* 169:5735–5744 (1987); Ohmori, et al., *Gene,* 28:159–170 (1984); Flower, et al., *Nuc. Acids Res.,* 14:8091–8101 (1986); Yin, et al., ibid., pp 6541–6549; and Maki, et al., *Proc. Natl. Acad. Sci. USA,* 80:7137–7141 (1983), which are hereby incorporated by reference. Using the nucleotide sequences, the protein subunits can be obtained by conventional recombinant DNA techniques. The availability of the substantially pure subunits makes possible the reconstitution of the polymerase core, γ complex clamp loader, and connected polymerase-clamp loader complexes using τ to connect them in accordance with the methods of the present invention. The β subunit can be added to the Pol III* subassembly to complete the structure of the Pol III holoenzyme, as described in Lasken, et al., *J. Bio Chem.,* 262:1720–1724 (1987), which is incorporated herein by reference. In addition, various components which do not include a particular subunit or subunits, such as the ε, θ, γ, χ, Ψ, and combinations thereof, can be assembled. Further, τ can be used in place of γ to form a clamp loader "τ complex" and its subassemblies. Finally, τ can be used to connect incomplete components of the core (i.e. no θ or no εθ) and γ complex (i.e. γδδ'Ψor γδδ'). In addition, τ can be used to replace γ and to connect "γ complex" (and less complete versions of τ complex) with the polymerase core (and less complete versions of the core).

Figure 2:
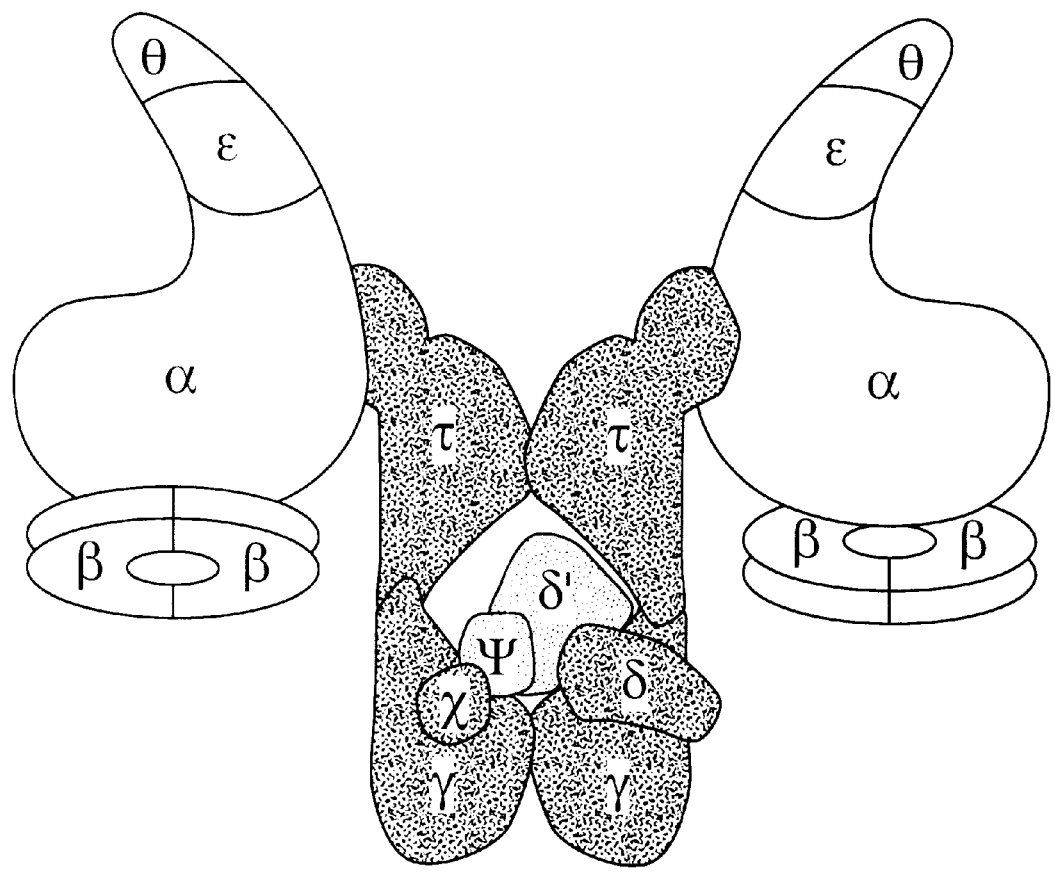
FIG. 2 is a schematic representation of the protein subunits in the $E.$ $coli$ three component DNA Pol III. The $\gamma$ complex (i.e. $\gamma\delta\delta'\chi\Psi$) and the two core polymerases (i.e. $\alpha\epsilon\theta$) are held together by a $\tau$ dimer, and the $\beta$ sliding clamp ring binds the core.

FIG. 2 shows the subunit contacts and stoichiometry of the 10-subunit Pol III assembly. Pol III can be constituted from individual pure proteins; it is the same size and is as active as Pol III purified naturally from *E. coli.* The particle contains 18 polypeptides in an arrangement consisting of two core polymerases and a γ complex clamp loader all connected to each other through τ, as illustrated in FIG. 1. Two core polymerases are bound to a τ dimer, most likely one on each promoter of τ. The τ dimer forms a heterotetramer with γ, and, assuming the tetramer is an isologous arrangement, the Pol III'-γ interaction is symmetric having a 2-fold rotational axis relating each unit [core-τ, promoter-γ promoter] to the other unit. However, the single copy each of δ, δ', χ, and Ψ imposes a structural asymmetry onto the structure of Pol III* such that there can be no overall 2-fold rotational axis. The β subunit associates with the α subunit of the core polymerase (Studwell-Vaughan, et al., *J. Biol. Chem.*, 266:19833–19841 (1991), which is hereby incorporated by reference), to form a single multiprotein particle referred to the Pol III holoenzyme.

Although the τ complex has not been purified from wild type *E. coli*, a τ complex and a γ-less form of Pol III* can be reconstituted from individual subunits, and these assemblies are active in replication assays, as discussed in Blinkova et al., *J. Bacteriol.*, 175:6018–6027 (1993), which is hereby incorporated by reference. Whether such complexes function in vivo is unknown, but it has been reported that *E. coli* cells are viable in which the signal for the −1 translational frameshift that produces γ is removed (Blinkova et al., *J. Bacteriol.*, 175:6018–6027 (1993), which is hereby incorporated by reference). These cells contain only the τ subunit and the γ-less Pol III, implying that γ-less Pol III can function at a replication fork.

The β subunit easily dissociates from the holoenzyme to form Pol III*, a subassembly of 9 different subunits. The Pol III* readily functions with β simply upon mixing them together. In addition to Pol III*, other subassemblies of the polymerase III holoenzyme may be useful, when employed with the β clamp, for achieving good DNA sequencing ladders. For example, the "γ-less Pol III*" subassembly, whose composition is postulated to be ((αεθ)$_4$τ$_4$ χΨδδ', contains the polymerase core complex αεθ and the clamp loading complex χΨδδ'; both attached to τ. γ-less Pol III*, which exhibits specific activity somewhat higher than either purified natural Pol III* or reconstituted Pol III*, can be formed by combining the component protein subunits in any order. In one procedure, the τχΨδδ' complex containing the clamp loader is formed first, followed by combination with α,ε, and θ subunits that comprise the polymerase core complex.

The just described τχΨδδ' complex can also be combined with the α polymerase subunit to form an ατχΨδδ' subassembly, a lower weight analog of γ-less Pol III*.

It may be desirable to form other relatively small subassemblies of the polymerase component, clamp loader component, and/or their connected versions (i.e. Pol III*) which would allow for simplified preparation and isolation procedures. For example, an active γδδ' or τδδ' clamp loader component can be constituted from three subunits, and the polymerase component can be limited to α alone or to only the αε subunits. Use of τ provides the ability to connect the components into the Pol III* and subassemblies of the Pol III*. For example, a τδδ' clamp loading component can be combined with the polymerase core component (i.e. αεθ) to form a connected αεθτδδ' subassembly. An even smaller Pol III* subassembly can be obtained by combining the τδδ' component with the polymerase unit α to form an ατδδ' complex.

These components are generally constituted from pure subunits produced by recombinant methods. They can also be purified in their natural state from cells or can be cloned such that two or more interacting subunits are coexpressed in one cell by recombinant techniques. The multi subunit complex can then be purified subsequent to its formation in the cell. These various techniques have been described in the published literature for subunits and components of prokaryotic and eukaryotic three component replicases Zuo et al., "DNA Polymerase Isolated From *Schizosaccharomyces pombe* Contains Five Subunits," *Proc. Natl. Acad. Sci USA,*. 94:11244–11249 (1997); McHenry, et al., "DNA Polymerase III Holoenzyme of *Escherichia coli.*, *J. Bio Chem.*, 252:6478–6484 (1977); Burgers et al., "Structure and Processivity of Two Forms of *Saccharomyces cerevisiae* DNA Polymerase*," *J. Biol. Chem.*, 273:19756–19762 (1998); Fien et al., "Identification of Replication Factor C From *Saccharomyces cerevisiae*: a Component of the Leading-Strand DNA Replication Complex," *Molec. Cell Biol.*, 12:155–163 (1992); and Gerik et al., "Overproduction and Affinity Purification of *Saccharomyces cerevisiae* Replication Factor C*," *J. Biol. Chem.*, 272:1256–1262 (1997); Kim et al., "In Vivo Assembly of Overproduced DNA Polymerase III," *J. Biol. Chem.* 271(34):20681–20689 (1996); Pritchard et al., "In Vivo Assembly of the τ-Complex of the DNA Polymerase III Holoenzyme Expressed from a Five-Gene Artificial Operon," *J. Biol. Chem.* 271(17):10291–10298 (1996); Ellison et al., "Reconstitution of Recombinant Human Replication Factor C (RFC) and Identification of an RFC Subcomplex Possessing DNA-dependent ATPase Activity," *J. Biol. Chem.* 273(10):5979–5987 (1998); and Rush et al., "The 44P Subunit of the T4 DNA Polymerase Accessory Protein Complex Catalyzes ATP Hydrolysis," *J. Biol. Chem.* 264(19):10943–10953 (1989), which are hereby incorporated by reference). These three component replicases are useful in DNA sequencing, and DNA amplification.

In the present invention, nucleic acid molecules may be amplified according to any of the literature-described manual or automated amplification methods. As used herein "amplification" refers to any in vitro method for increasing the number of copies of a nucleotide sequence with the use of a DNA polymerase. Nucleic acid amplification results in the incorporation of nucleotides into a DNA molecule or primer thereby forming a new DNA molecule complementary to a DNA template. The formed DNA molecule and its template can be used as templates to synthesize additional DNA molecules. As used herein, one amplification reaction may consist of many rounds of DNA replication. DNA amplification reactions include, for example, polymerase chain reactions ("PCR"). One PCR reaction may consist of 20 to 100 "cycles" of denaturation and synthesis of a DNA molecule. Such methods include, but are not limited to, PCR (as described in U.S. Pat. Nos. 4,683,195 and 4,683,202, which are hereby incorporated by reference), Strand Displacement Amplification ("SDA")(as described in U.S. Pat. No. 5,455,166, which is hereby incorporated by reference), and Nucleic Acid Sequence-Based Amplification ("NASBA")(as described in U.S. Pat. No. 5,409,818, which is hereby incorporated by reference). For example, amplification may be achieved by a rolling circle replication system which may even use a helicase for enhanced efficiency in DNA melting without heat (see Yuzhakou et al., "Replisome Assembly Reveals the Basis for Asymmetric Function in Leading and Lagging Strand Replication," *Cell* 86:877–886 (1996) and Mok et al., "The *Escherichia coli* Preprimosome and DnaB Hilicase Can Form Replication Forks That Move at the Same Rate," *J. Biol. Chem.* 262:16558–16565 (1987), which are hereby incorporated by reference). Most preferably, nucleic acid molecules are amplified by the methods of the present invention using PCR-based amplification techniques.

For example, the present process involves a chain reaction for producing, in exponential quantities relative to the number of reaction steps involved, at least one specific nucleic acid sequence, given (a) that the ends of the required sequence are known in sufficient detail that oligonucleotides can be synthesized which will hybridize to them and (b) that a small amount of the sequence is available to initiate the chain reaction. The product of the chain reaction will be a discrete nucleic acid duplex with termini corresponding to the ends of the specific primers employed.

Any source of nucleic acid, in purified or nonpurified form, can be utilized as the starting nucleic acid or acids, provided it is suspected of containing the specific nucleic acid sequence desired. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the β-globin gene contained in whole human DNA or a portion of nucleic acid sequence due to a particular microorganism which organism might constitute only a very minor fraction of a particular biological sample. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules.

The nucleic acid or acids may be obtained from any source, for example, from plasmids such as pBR322, from cloned DNA or RNA, or from natural DNA or RNA from any source, including bacteria, yeast, viruses, and higher organisms such as plants or animals. DNA or RNA may be extracted from blood, tissue material such as corionic villi or amniotic cells by a variety of techniques such as that described by Maniatis et al., *Molecular Cloning: A Laboratory Manual*, (New York: Cold Spring Harbor Laboratory) pp 280–281 (1982).

Any specific nucleic acid sequence can be produced by the present process. It is only necessary that a sufficient number of bases at both ends of the sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater the specificity of the primers for the target nucleic acid sequence, and, thus, the greater the efficiency of the process. It will be understood that the word primer as used hereinafter may refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code will be used for each strand. One primer from this collection will be homologous with the end of the desired sequence to be amplified.

The oligonucleotide primers may be prepared using any suitable method, such as, for example, the phosphotriester and phosphodiester methods described above or automated embodiments thereof. In one such automated embodiment diethylophosphoramidites are used as starting materials and may be synthesized as described by Beaucage et al., *Tetrahedron Letters*, 22:1859–1862 (1981), which is hereby incorporated by reference. One method for synthesizing oligonucleotides on a modified solid support is described in U.S. Pat. No. 4,458,006, which is hereby incorporated by reference. It is also possible to use a primer which has been isolated from a biological source (such as a restriction endonuclease digest).

The specific nucleic acid sequence is produced by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable denaturing method including physical, chemical, or enzymatic means. One physical method of separating the strands of the nucleic acid involves heating the nucleic acid until it is completely (>99%) denatured. Typical heat denaturation may involve temperatures ranging from about 80° to 105° C. for times ranging from about 1 to 10 minutes. Strand separation may also be induced by an enzyme from the class of enzymes known as helicases or the enzyme RecA, which has helicase activity and, in the presence of riboATP, is known to denature DNA. The reaction conditions suitable for separating the strands of nucleic acids with helicases are described by *Cold Spring Harbor Symposia on Quantitative Biology*, Vol. XLIII "DNA: Replication and Recombination" (New York: Cold Spring Harbor Laboratory, 1978), and techniques for using RecA are reviewed in C. Radding, *Ann. Rev. Genetics*, 16:405–37 (1982), which is hereby incorporated by reference.

If the original nucleic acid containing the sequence to be amplified is single stranded, its complement is synthesized by adding one or two oligonucleotide primers thereto. If an appropriate single primer is added, a primer extension product is synthesized in the presence of the primer, an agent for polymerization, and the four nucleotides described below. The product will be partially complementary to the single-stranded nucleic acid and will hybridize with the nucleic acid strand to form a duplex of unequal length strands that may then be separated into single strands, as described above, to produce two single separated complementary strands. Alternatively, two appropriate primers may be added to the single-stranded nucleic acid and the reaction is carried out.

If the original nucleic acid constitutes the sequence to be amplified, the primer extension product(s) produced will be completely complementary to the strands of the original nucleic acid and will hybridize therewith to form a duplex of equal length strands to be separated into single-stranded molecules.

When the complementary strands of the nucleic acid or acids are separated, whether the nucleic acid was originally double or single stranded, the strands are ready to be used as a template for the synthesis of additional nucleic acid strands. This synthesis can be performed using any suitable method. Generally, it occurs in a buffered aqueous solution, preferably at a pH of 7–9, most preferably about 8. Preferably, a molar excess (for cloned nucleic acid, usually about 1000:1 primer:template, and for genomic nucleic acid, usually about $10^6$:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP, and TTP are also added to the synthesis mixture in adequate amounts, and the resulting solution is heated to about 90°–100° C. for about 1 to 10 minutes, preferably from 1 to 4 minutes. After this heating period, the solution is allowed to cool to from 20°–60° C., which is preferable for the primer hybridization. To the cooled mixture is added the Pol III-type polymerase, and the reaction is allowed to occur under conditions known in the art. This synthesis reaction may occur at from room temperature up to 90° C., preferably 72° C., using either thermolabile or thermostable DNA Pol III-type enzyme system.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

New nucleic acid is synthesized on the single-stranded molecules. Additional inducing agent, nucleotides, and primers may be added if necessary for the reaction to proceed under the conditions prescribed above. Again, the synthesis will be initiated at one end of the oligonucleotide primers and will proceed along the single strands of the template to produce additional nucleic acid. After this step, half of the extension product will consist of the specific nucleic acid sequence bounded by the two primers.

The steps of strand separation and extension product synthesis can be repeated as often as needed to produce the desired quantity of the specific nucleic acid sequence. As will be described in further detail below, the amount of the specific nucleic acid sequence produced will accumulate in an exponential fashion.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

The present invention can be performed in a step-wise fashion where after each step new reagents are added, or simultaneously, where all reagents are added at the initial step, or partially step-wise and partially simultaneous, where fresh reagent is added after a given number of steps. If a method of strand separation, such as heat, is employed which will inactivate the agent for polymerization, as in the case of a heat-labile enzyme, then it is necessary to replenish the agent for polymerization after every strand separation step. The simultaneous method may be utilized when a number of purified components, including an enzymatic means such as helicase, is used for the strand separation step. In the simultaneous procedure, the reaction mixture may contain, in addition to the nucleic acid strand(s) containing the desired sequence, the strand-separating enzyme (e.g., helicase), an appropriate energy source for the strand-separating enzyme, such as rATP, the four nucleotides, the oligonucleotide primers in molar excess, and the three component polymerase. If heat is used for denaturation in a simultaneous process, a thermostable three component polymerase may be employed which will operate at an elevated temperature, preferably 65°–90° C., depending on the inducing agent, at which temperature the nucleic acid will consist of single and double strands in equilibrium. For smaller lengths of nucleic acid, lower temperatures of about 50° C. may be employed. The upper temperature will depend on the temperature at which the three component polymerase will degrade or the temperature above which an insufficient level of primer hybridization will occur. Each step of the process will occur sequentially notwithstanding the initial presence of all the reagents. Additional materials may be added as necessary. After the appropriate length of time has passed to produce the desired amount of the specific nucleic acid sequence, the reaction may be halted by inactivating the enzymes in any known manner or separating the components of the reaction.

Thus, in amplifying a nucleic acid molecule according to the present invention, the nucleic acid molecule is contacted with a composition comprising a thermolabile or thermostable three component polymerase. The three component polymerase used in the present methods are preferably substantially reduced in 3'–5' exonuclease activity (i.e., they are "exo–"), for reasons explained in detail in the Examples below. Most preferable for use in the present methods is the E. coli three component polymerase in which the β clamp component is added to an assembly containing the other two components in which the clamp loader is attached to the polymerase component using the τ subunit, and the γ subunit is omitted. The three component polymerase is used in the present methods at concentrations of about 0.01–400 μg/milliliter, preferably about 1–80 μg/milliliter, and most preferably about 2–20 μg/milliliter.

In an alternative preferred embodiment, the invention provides methods of amplifying large nucleic acid molecules, by a technique commonly referred to as "long PCR" (Barnes, W. M., Proc. Natl. Acad. Sci. USA, 91:2216–2220 (1994) ("Barnes"); Cheng, S. et. al., Proc. Natl. Acad. Sci. USA, 91:5695–5699 (1994), which are hereby incorporated by reference). In such a method, useful for amplifying nucleic acid molecules larger than about 5–6 kilobases, the composition with which the target nucleic acid molecule is contacted comprises not only three component polymerase, but also comprises a low concentration of the DNA polymerase component (preferably thermostable polymerases), exhibiting the 3'–5' exonuclease activity ("exo+" polymerases), at concentrations of about 0.0002–200 units per milliliter, preferably about 0.002–100 units per milliliter, more preferably about 0.002–20 units per milliliter, even more preferably about 0.002–2.0 units per milliliter, and most preferably at concentrations of about 0.40 units per milliliter. Preferred exo+polymerases for use in the present methods are Pfu/DEEPVENT or Tli/NENT™ (Barnes; U.S. Pat. No. 5,436,149, which are hereby incorporated by reference); thermostable polymerases from Thermotoga species such as Tma (U.S. Pat. No. 5,512,462, which is hereby incorporated by reference); and certain thermostable polymerases and mutants thereof isolated from Thermotoga neaPolitana such as Tne(3'exo+). By using such compositions comprising a three component polymerase and an exo+ polymerase in the present methods, DNA sequences of at least 35–100 kilobases in length may be amplified to high concentrations with significantly improved fidelity.

In another embodiment of the present invention, nucleic acid molecules may be sequenced according to any of the literature-described manual or automated sequencing methods. Such methods include, but are not limited to, dideoxy sequencing methods ("Sanger sequencing"; Sanger, F., et al., *J. Mol. Biol.,* 94:444–448 (1975); Sanger, F., et al., *Proc. Natl. Acad. Sci. USA,* 74:5463–5467 (1977); U.S. Pat. Nos. 4,962,022 and 5,498,523, which are hereby incorporated by reference), as well as by PCR based methods and more complex PCR-based nucleic acid fingerprinting techniques such as Random Amplified Polymorphic DNA ("RAPD") analysis (Williams, J. G. K., et al., *Nucl. Acids Res.,* 18(22):6531–6535, (1990), which is hereby incorporated by reference), Arbitrarily Primed PCR ("AP-PCR") (Welsh, J., et al., *Nucl. Acids Res.,* 18(24):7213–7218, (1990), which is hereby incorporated by reference), DNA Amplification Fingerprinting ("DAF")(Caetano-Anollés et al., *Bio/Technology,* 9:553–557, (1991), which is hereby incorporated by reference), microsatellite PCR or Directed Amplification of Minisatellite-region DNA ("DAMD") (Heath, D.D., et al., *Nucl. Acids Res.,* 21(24): 5782–5785, (1993), which is hereby incorporated by reference), and Amplification Fragment Length Polymorphism ("AFLP") analysis (Vos, P., et al., *Nucl. Acids Res.,* 23(21):4407–4414 (1995); Lin, J. J., et al., *FOCUS,* 17(2):66–70, (1995), which are hereby incorporated by reference).

As described above for amplification methods, in sequencing a nucleic acid molecule according to the methods of the present invention, the nucleic acid molecule is subjected to a nucleic acid sequencing process with a three component polymerase. As in the amplification methods, three component polymerases used in the nucleic acid sequencing methods of the present invention are preferably substantially reduced in 3'–5' exonuclease activity; most preferable for use in the present method is a three component polymerase which lacks the ε, θ and γ subunits of the native enzyme. Three component polymerases used for nucleic acid sequencing according to the present method are used at the same preferred concentration ranges described above for nucleic acid amplification.

Once the nucleic acid molecule to be sequenced is contacted with the three component polymerase, the sequencing reactions may proceed according to the protocols disclosed in the above-referenced techniques, with the same adjustments in thermolabile enzyme addition and cycle time noted above for amplification techniques.

In other preferred embodiments, the invention provides kits for use in nucleic acid amplification or sequencing, utilizing three component polymerase according to the present methods.

A DNA amplification kit according to the present invention comprises a three component polymerase and a deoxynucleoside triphosphate. The amplification kit encompassed by this aspect of the present invention may further comprise additional reagents and compounds necessary for carrying out standard nucleic amplification protocols (See U.S. Pat. Nos. 4,683,195 and 4,683,202, which are directed to methods of DNA amplification by PCR).

Similarly, a DNA sequencing kit according to the present invention comprises a three component polymerase and a dideoxynucleoside triphosphate. The sequencing kit may further comprise additional reagents and compounds necessary for carrying out standard nucleic sequencing protocols, such as pyrophosphatase, agarose or polyacrylamide media for formulating sequencing gels, and other components necessary for detection of sequenced nucleic acids (See U.S. Pat. Nos. 4,962,020 and 5,498,523, which are directed to methods of DNA sequencing).

The three component polymerase contained in the amplification and sequencing kits is preferably a thermolabile or a thermostable three component polymerase and, more preferably, a three component polymerase that is substantially reduced in 3'–5' exonuclease activity. Most preferable for use in these amplification and sequencing kits is a three component polymerase complex lacking the ε subunit of the *E. coli* three component polymerase.

In additional preferred embodiments, the amplification and sequencing kits of the invention may further comprise a DNA polymerase having 3'-5' exonuclease activity ("exo+" polymerases). Preferred such exo+polymerases are Pfu/DEEPVENT, TliNENT™, Tma, Tne(3'exo+), and mutants and derivatives thereof

EXAMPLES

Example 1

Preparation of αετδδ' χΨ

A mixture containing 944 μg υ, 442 μg χ, and 202 μg Ψ was incubated in a final volume of 1.39 ml Buffer A (20 mM DDT, 0.5 mM EDTA, 10% glycerol) for 30 min. at 15° C. This mixture was then added to a solution containing 492 μg δ' and 772 μg δ which had been preincubated together in 1.31 ml Buffer A for 30 min. at 15° C. This mixture of five subunits was incubated another 30 min. at 15° C. to form the τδδ' χΨ clamp loader (i.e. τ complex). The polymerase component was made by mixing 2,586 μg α with 821 μg ε in a volume of 5.59 ml Buffer A and incubated 30 min. at 15° C. Then, the polymerase component was mixed with the τ complex clamp loader component and incubated a further 30 min. at 15° C. to form αετδδ' χΨ. This mixture was then loaded onto a 1 ml MonoQ column and eluted with a 4 ml 0–0.4 M gradient of NaCl in Buffer A, collecting 20 drop fractions. The αετδδ' χΨ complex resolved from excess subunits and subassemblies. Fractions 45–47 containing approximately 1.5 mg protein in 1.7 ml were aliquoted separately (not pooled) and stored at –70° C. (fractions 45,46,47 were 1.06, 0.98 and 0.67 mg/ml, respectively).

Example 2

Preparation of ατδδ' χΨ

A mixture containing 1.89 μg τ, 883 μg χ, and 405 μg Ψ were mixed in 2.78 ml Buffer A and incubated 30 min. at 15° C. A solution containing 1.54 μg δ and 0.98 μg δ' in 2.62 ml Buffer A which had been preincubated for 30 min. at 15° C. was then added to form the T complex clamp loader. To this was added 5.17 μg α (polymerase component) in 2.07 ml Buffer A followed by incubation for 30 min. at 15° C. to form ατδδ χΨ complex. The ατδδ χΨ complex was purified from unbound subunits on a 1 ml MonoQ column eluted with a gradient of 0 to 0.4 M NaCl in 40 ml Buffer A collecting 20 drop fractions. Fractions 48–50 contained ατδδ χΨ and were aliquoted separately and stored at –70° C. Fractions 48–50 were 1.56, 1.02, and 1.32 mg/ml, respectively.

Example 3

DNA Sequencing Reactions

The sequencing reaction was performed by mixing 7.5 μl containing 0.7 μg M13mp18 single stranded DNA and 1 pmol DNA oligonucleotide primer in 40 mM Tris-HCl (pH 7.5), 30 mM MgCl$_2$, 25 mM NaCl with 2 µl label mix (1.5 µM each of dCTP, dGTP, dTTP, 50 mM DTT, and 8 mM ATP), and 0.5 µl [α-$^{35}$S] dATP. To this was added 6 µl containing 3.2 µg SSB, 0.42 µg β (containing 0.125 µl pyrophosphatase in 20 mM Tris-HCl (pH 7.5), 0.5 mM EDTA, 2 mM DTT and 40 µg/ml BSA) and 0.8 µg ατδδ χΨ (final volume 15.5 µl). This reaction was incubated for 5 min. at room temperature. Next, four 3.5 aliquots were removed and proportioned into four tubes that each contained 2.5 µl of 80 µM each of dATP, dCTP, dGTP, dTTP, and contained either: 64 µM ddATP (A reaction), 64 µM ddCTP (C reaction), 64 µM ddGTP (G reaction), or 64 µM ddTTP (T reaction). After incubation for 5 min. at 37° C., the four reactions were quenched by adding 4.5 µl stop solution containing 0.2% SDS and 50 mM EDTA. Then, 0.5 µl of proteinase K (10 mg/ml) was added and incubated at 65° C. for 20 min. Reactions were loaded onto 8% DNA sequencing polyacrylamide gels cast in Tris/Borate/EDTA buffer followed by electrophoresis. Gels were removed, dried, and exposed to X-ray film. Several reactions similar to that described above were performed with the following variations. The type of DNA polymerase/clamp loader was varied (i.e., α(0.38 µg)+γδδ' χΨ (0.37 µg), α(0.38 µg)+τδδ' χΨ (0.47 µg), ατ (mix of 0.38 µg α and 0.21 µg τ)+γδδ' χΨ (0.37 µg), α (0.38 µg)+γδδ' (0.32 µg), ατ(mixture of 0.38 µg α and 0.21 µg τ)+γδδ' (0.32 µg)). In these reactions, these enzymes and complexes were first mixed at a 10-fold higher concentration than noted, and in a volume of 10 µl. Then, 1 µl was added to the sequencing reaction to give the concentration in the reaction noted above.

Figure 3:
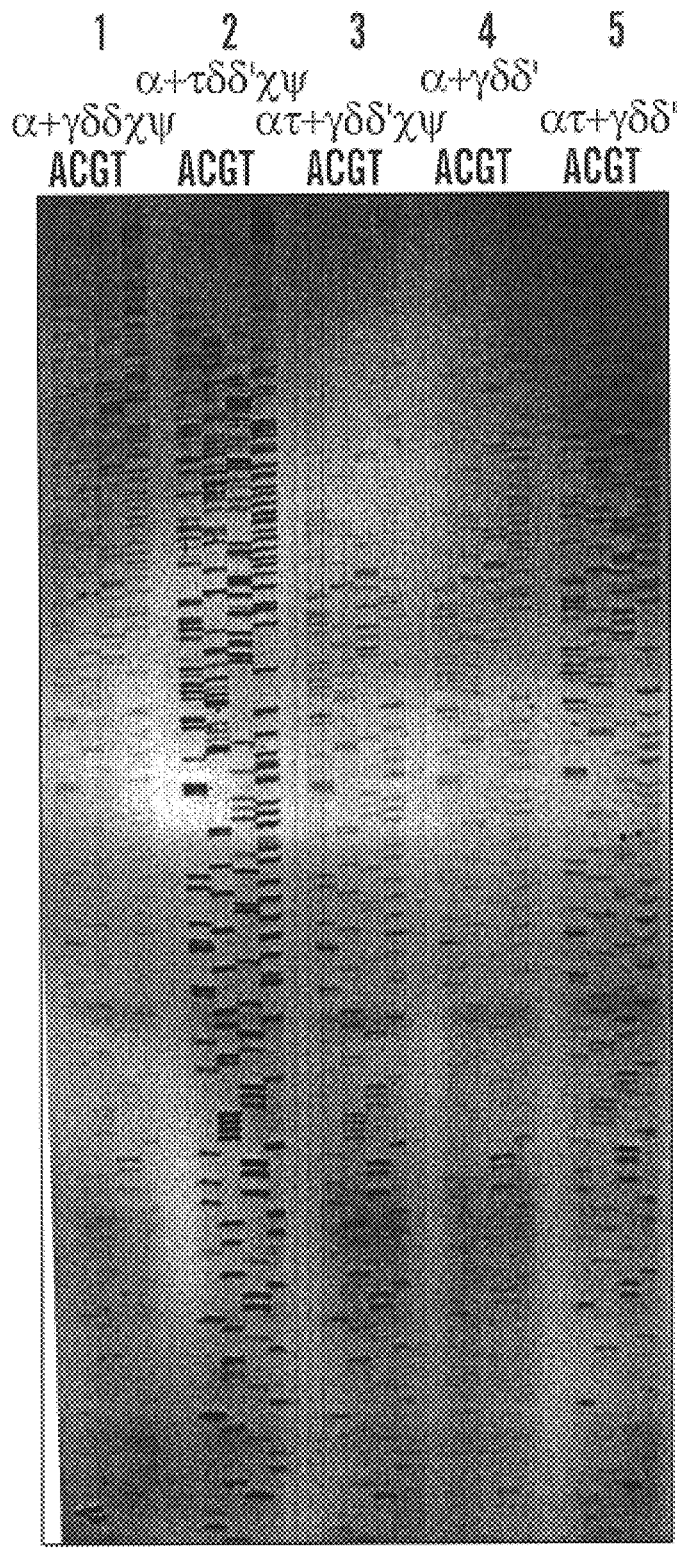
FIG. 3 shows DNA sequencing ladders produced using different enzyme forms where the three components are either individual, or where the polymerase and clamp loader components are part of one complex. The sequencing reactions were produced using $\beta$ clamp SSB and either: 1) $\alpha$ plus $\gamma$ complex; 2) $\alpha$ plus $\tau$ complex (i.e. forms $\alpha\tau\delta\delta'\chi\gamma$ in which the polymerase and clamp loader are connected by $\tau$; 3) does not connect the components since $\gamma$ is in the preassembled clamp loader; 4) $\alpha+\gamma\delta\delta'$; and 5) $\alpha\tau+\gamma\delta\delta'$ ($\tau$ does not connect the components since $\gamma$ is in the preassembled clamp loader). Each experiment consists of 4 lanes in which the dideoxynucleoside triphosphate used in the reaction is indicated at the top of the gel.

The results of Examples 1 to 3 are shown in FIG. 3. In sum, all of these reactions and the variations thereof produced DNA sequencing ladders, showing the tolerance in use of this enzyme to a variety of conditions. For example, the two components (i.e. DNA polymerase and clamp loader) do not need to be connected together. Nonetheless, connection of these two components would appear to give better results compared to use of the individual three components (at least under the specific conditions of this experiment). Bands representing all, or nearly all, of the individual nucleotide positions are preseit in the sequencing gels. An important point to note is that enzyme forms that contained the ε subunit (i.e. the 3'-5' exonuclease) did not give good sequencing ladders. Enzyme with fully active ε subunit gave ladders that were missing several intermediate bands.

Figure 4:
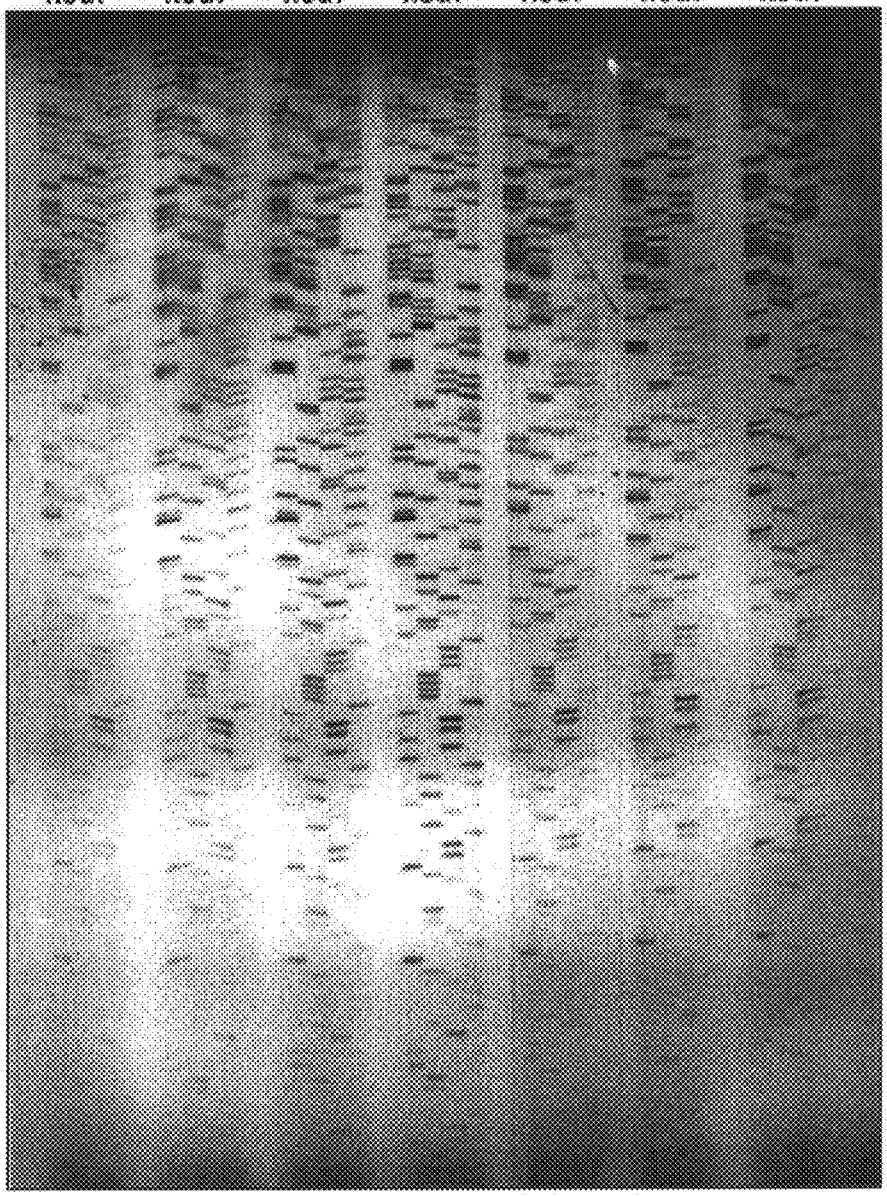
FIG. 4 shows DNA sequencing ladders using $\alpha\tau\delta\delta'\chi\Psi$. The sequencing reactions were produced using: 1) 8 $\mu$M ddNTP, 1.6 $\mu$g $\alpha\tau\delta\delta'\chi\Psi$ 0.42 $\mu$g $\beta$ and 3.2 $\mu$g SSB; 2) 16 $\mu$M ddNTP, 1.6 $\mu$g $\alpha\tau\delta\delta'\chi\Psi$, 0.42 $\mu$g $\beta$, 3.2 $\mu$g SSB; 3) 32 $\mu$M ddNTP, 1.6 $\mu$g $\alpha\tau\delta\delta'\chi\Psi$, 0.42 $\mu$g $\beta$, 3.2 $\mu$g SSB; 4) 64 $\mu$M ddNTP, 1.6 $\mu$g $\alpha\tau\delta\delta'\chi\Psi$ 0.42 $\mu$g $\beta$, 3.2 $\mu$g SSB; 5) 16 $\mu$M ddNTP, 0.8 $\mu$g $\alpha\tau\delta\delta'\chi\Psi$, 0.42 $\mu$g $\beta$, 3.2 $\mu$g SSB; 6) 16 $\mu$M ddNTP, 0.4 $\mu$g $\alpha\tau\delta\delta'\chi\Psi$, 0.42 $\mu$g $\beta$, 3.2 $\mu$g SSB; and 7) 16 $\mu$M ddNTP, 1.6 $\mu$g $\alpha\tau\delta\delta'\chi\Psi$, 0.42 $\mu$g $\beta$, 1.6 $\mu$g SSB. Each experiment consists of 4 lanes in which the ddNTP used in the reaction is indicated by either A,C,G, or T.

In a subsequent experiment the ατδδ χΨ complex was used along with β and SSB. In this set of experiments the amounts of SSB, ατδδ χΨ, and dNTP concentration was varied. All other conditions were essentially as described above (see Detailed Description of Drawings for details). The amount of SSB was varied from 1.6 µg to 3.2 µg, the amount of ατδδ χΨ was varied from 0.4 µg to 1.6 µg, and the concentration of ddNTP was varied from 8 µM to 64 µM. The results of the series of experiments are shown in FIG. 4. In summary, the best results were obtained using ddNTP at 16 µM or above, ατδδ χΨ at 1.6 µg, and SSB at 3.2 µg.

Example 4

PCR Using *E. coli* Pol III with or without ε Subunit

A M13mp18 ssDNA template was used to perform the polymerase chain reaction with a three component polymerase and to characterize the reaction products. The starting reaction mixture of 150 microliters contained 1.7 micrograms M13mp18 ssDNA in 20 millimolar Tris-HCl (pH 7.5), 8 millimolar MgCl$_2$, 4% glycerol, 5 millimolar DTT, 0.5 millimolar ATP, 180 micromolar each of dATP, dGTP, dCTP, and 60 microimolar $^{32}$P-dTTP. To this reaction was added 48 micrograms *E. coli* SSB.

The reaction also contained 2 micromolar of a DNA 20 mer (5'-GCTTTTGCGGGATCGTCACC-3' (SEQ. ID. No. 1); map position 1395 to 1376 on M13). To this reaction was added 1 microgram β and 2 micrograms of either αετδδ'χΨ or ατδδ'χΨ. The reaction was incubated at 30° C. for 5 min. to complete cycle one and then 15 microliters of the second primer (5 '-CGATATTTGAAGTCTTTCGG-3' (SEQ. ID. No. 2); map position 349 to 368 on M13) that anneals about 1 kb downstream was added. To perform the second through sixth cycles, the reaction was heated to 94° C. for 45s then cooled to 30° C. and β (1 microgram) and 2 micrograms of either αετδδ'χΨ or ατδδ'χΨ was added and incubation was continued for 5 min. This was repeated for each cycle. At the end of each cycle, 20 microliters was removed and added to 20 microliters of 1% SDS, 40 millimolar EDTA. At the end of six cycles, the quenched samples were analyzed in a 0.8% neutral agarose gel. After electrophoresis, the neutral gel was analyzed for ethidium bromide induced fluorescence, photographed, and then dried and exposed to X-ray film.

The expected results of each cycle are as follows. In the first cycle, the first primer should be extended approximately 7.2 kb around the entire circle of the M13mp18 template (see FIG. 5). In the second cycle, the two strands are separated and the second primer anneals to the product (7.2 kb linear) of the first cycle which, upon extension, yields a duplex segment of approximately 1 kb (the distance between the two primers including the primers themselves [actually 1046 nucleotides]). In this cycle, as in all cycles, the circle is primed and extended to produce another circular duplex. The third cycle results in the first time that a 1 kb duplex segment is produced by extension of primer 1 that annealed to the 1 kb strand produced by extension of primer 2 in the second cycle. The other two products include one duplex circle and two 7.2 kb linear ssDNAs that have a 1 kb section of duplex formed by extension of primer 2. The third cycle also produces another circular duplex. Cycles 4–6 result in production of 3, 7, and 18 molecules of 1 kb duplex, respectively from each molecule of M1 3mpl 8 circular DNA. Products of these cycles are shown in the scheme in FIG. 5. Overall, the PCR amplified product is the approximately 1 kb duplex.

Figure 6:
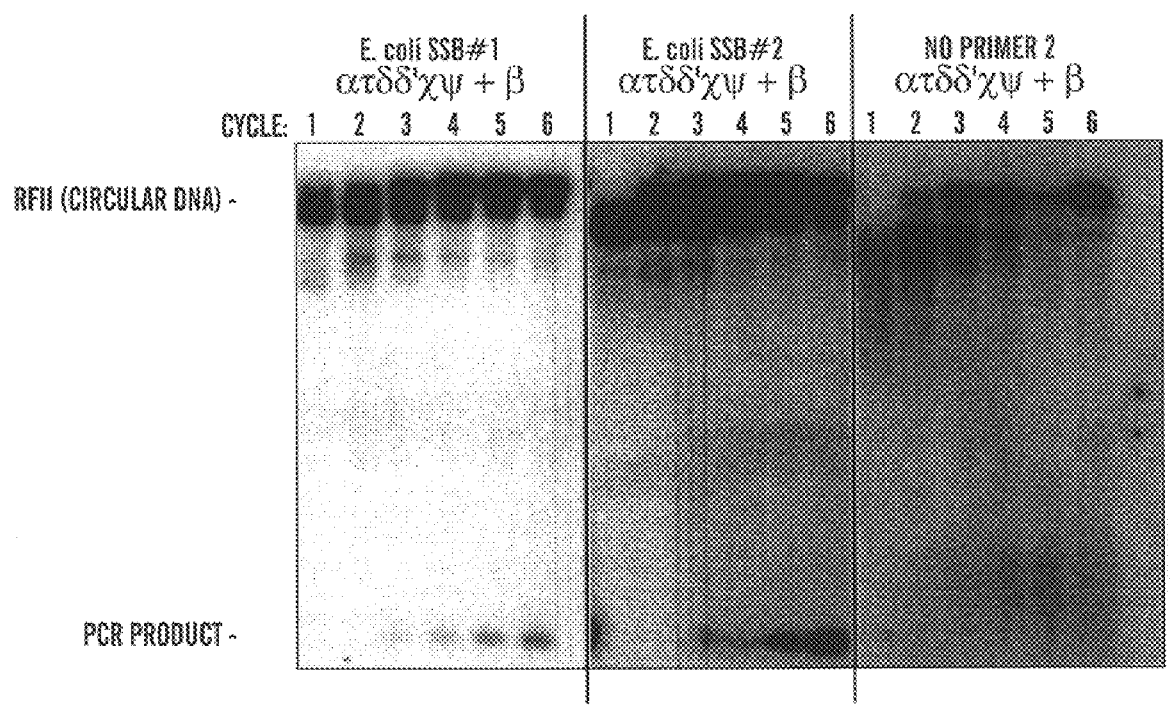
FIG. 6 is an autoradiogram of a native agarose gel of the reaction products during the cycles of a PCR reaction using $E.$ $coli$ SSB and the three component polymerase consisting of the $\beta$ subunit and the clamp loader connected to the polymerase in the $\alpha\tau\delta\delta'\chi\Psi$ complex. The cycle numbers are noted at the top of the gel, and the positions of the circular duplex product and the amplified product are noted to the left. Two examples of PCR reactions are shown in the first two sets, and the last set is a reaction performed in the absence of primer 2.

The results of these reactions produced the expected 1 kb PCR product using the enzyme lacking ε(ατδδ'χΨ). The αετδδ'χΨ produced the circular duplex DNA, but did not produce a significant amount of the expected 1 kb duplex PCR product (FIG. 6). Examination of the ethidium bromide induced fluorescence in the native gel yielded a possible reason for the failure of the ε containing enzyme to form the PCR product. The primers used in the PCR reaction can be observed in the neutral agarose gel as they induce fluorescence of the ethidium bromide. The fluorescence signal caused by the primers decreases significantly with each cycle of amplification using the αετδδ'χΨ enzyme. Presumably, the 3'-5'-exonuclease activity of the ε subunit degraded the oligonucleotide primers. Degradation of the primers, essential for PCR, prevented formation of the 1 kb PCR amplification product.

The autoradiogram of the native gel showing the results of the experiment using ατδδ'χΨ is shown in FIG. 6. The first cycle produces the circular duplex. The 1 kb product is not present in cycles 1 and 2 as predicted from the path of amplification of FIG. 5. The 1 kb product is only just detectable after cycle 3 and increases exponentially thereafter.

These results indicate that the *E. coli* three component polymerase has too high of an exonuclease activity for these reactions. It may be presumed that some exonuclease activity can be tolerated, as some enzymes currently in use for PCR contain 3'–5' exonuclease activity. Probably, the problem experienced here is exaggerated by the need to add polymerase back to the reaction at each step. This will result in a continued buildup of the δ subunit in the reaction mixture. As the ε subunit is documented to refold after denaturization using guanidine hydrochloride (Scheuermann, R. H. et al., Proc. Natl. Acad. Sci. USA 81:7747–7751 (1985), which is hereby incorporated by reference), it seems possible that ε may also refold after heat denaturization thereby resulting in more and more exonuclease activity present in the reaction as amplification cycles continue due to the repeated additions of enzyme after each cycle.

The proofreading 3'–5' exonuclease activity is an attractive action to have present during amplification as it proofreads the product of the polymerase thereby reducing the number of mistakes that accumulate during the amplification process (i.e., by reducing the retention of polymerization errors). Hence, the use of a three component polymerase that contains less 3'–5' exonuclease activity (such as use of a ε mutant that has less 3'–5' exonuclease activity) could be used in PCR reactions to enhance the fidelity of the overall process. It is possible that the inherent proofreading activity could be tolerated if addition of enzyme containing the proofreading nuclease were not needed at every step. With this in mind, use of thermophilic three component polymerase containing the proofreading activity, that is thermostabile and, therefore, does not need to be added at each step, will result in formation of amplified product.

Example 5
PCR Amplification Using Thermostable SSB

The PCR experiments of FIG. 6 utilized E. coli SSB. The SSB was not added at each cycle as β and Pol III* were. Hence, even though SSB is generally regarded as a heat stable protein, it is possible it becomes partially inactivated during these amplification procedures. To circumvent this possible problem, the SSB from a thermophilic bacterium, Aquifex aeolicus, was cloned from the known sequence (Deckert et al., "The Complete Genome of the Hyper-Thermophilic Bacteria Aquifex aeolicus," Nature 392:353–358 (1998), which is hereby incorporated by reference). The gene encoding A. aeolicus SSB was amplified using PCR and placed into a PET vector downstream of a T7 promotor. The plasmid was introduced into an E. coli BL21 strain containing the gene for the T7 RNA polymerase. Following IPTG induction, the SSB was purified by lysing cells by pressure, the lysate was heated to 65° C. for 20 min., and, then, SSB was purified from the supernatant using ion exchange chromatography on DEAE Sephacel and then on Heparin Agarose.

Figure 7:
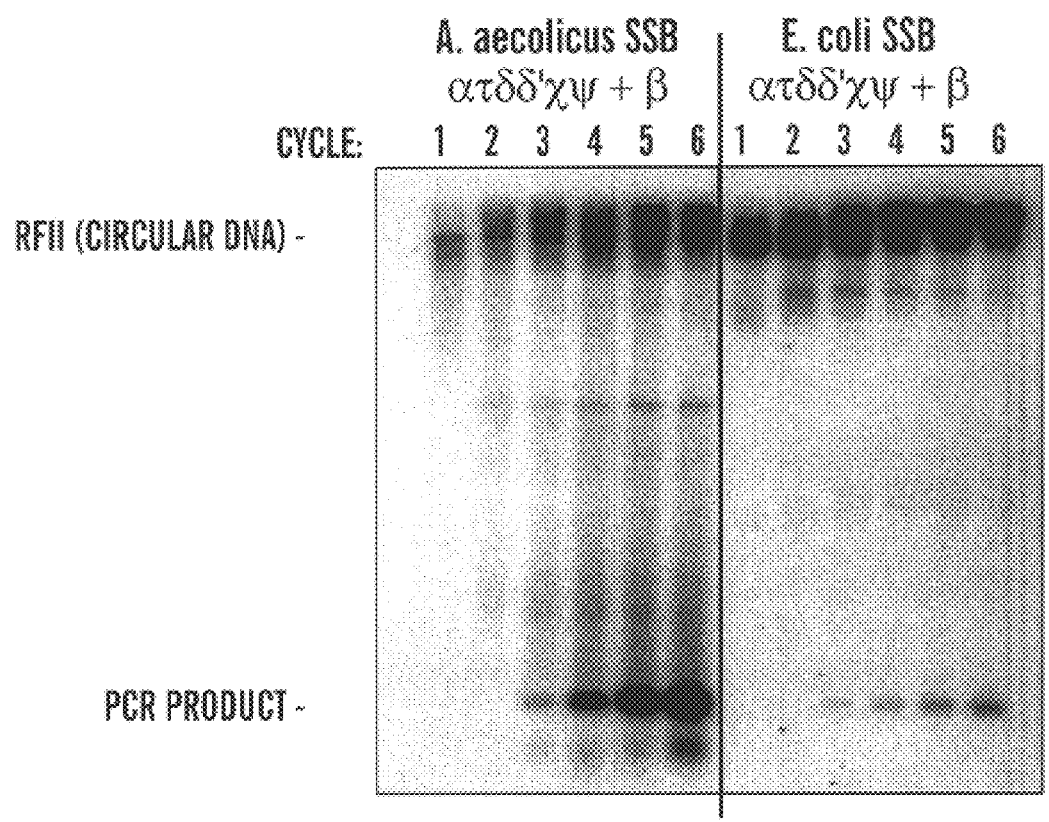
FIG. 7 is a comparison of PCR products produced using either $A.$ $aecolicus$ SSB or $E.$ $coli$ SSB. Cycle numbers are identified on the top of the autoradiogram of the native gel. In each case, the clamp loader and polymerase components were added as the complex ($\alpha\tau\delta\delta'\chi\Psi$ complex), and the $\beta$ clamp was added as a separate protein.

PCR reactions were performed as described in Example 5 using either 48 micrograms E. coli SSB or 45 microgram A. aeolicus SSB. The β (1 microgram) and ατδδ'χΨ (2 micrograms) were added at each cycle. The autoradiogram of the native agarose gel is shown in FIG. 7. The result shows much more 1 kb PCR product in the reaction using the thermostable SSB compared to use of E. coli SSB.

Example 6
Characterization of Exponential Product Formation

Figure 5:
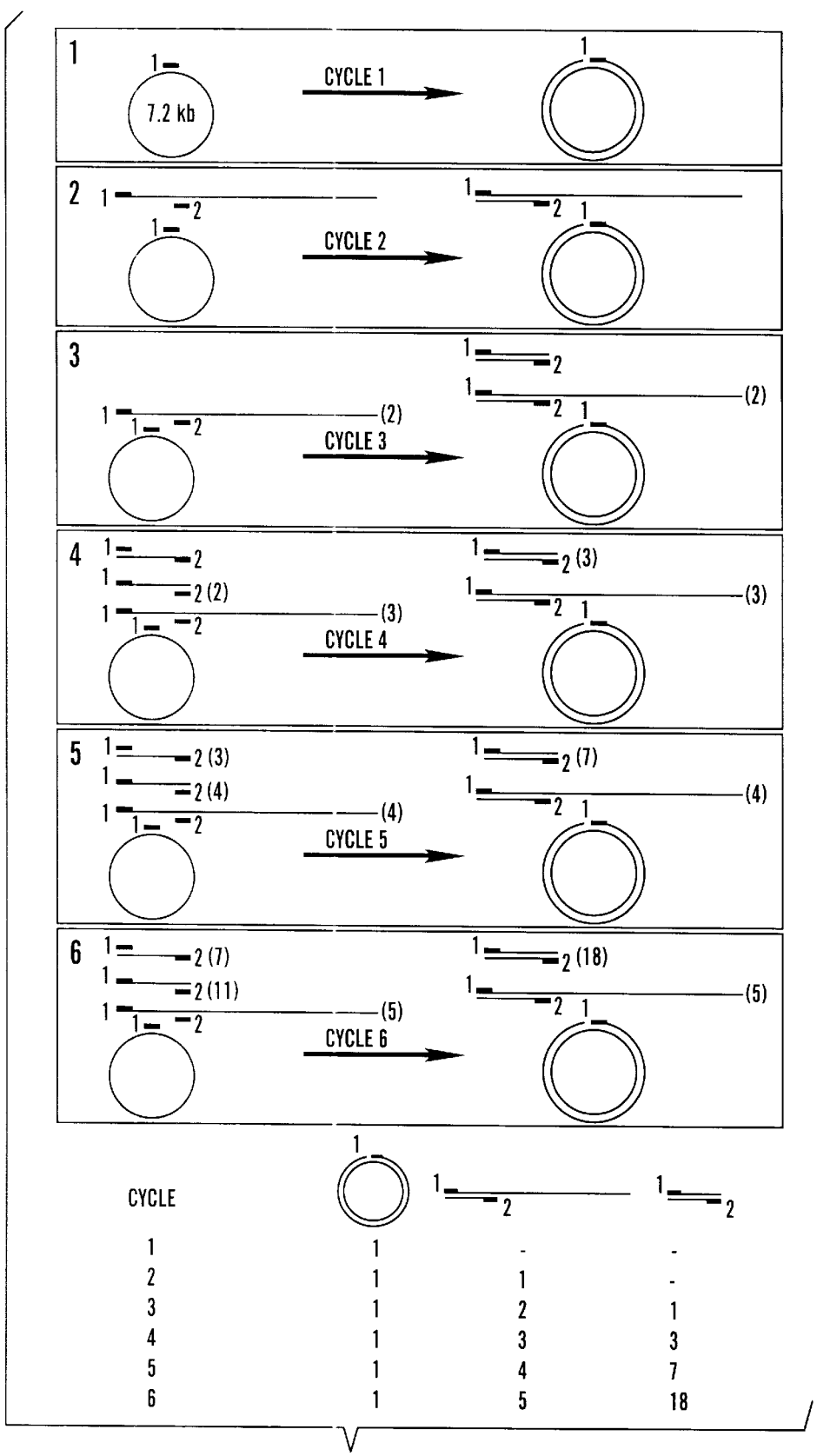
FIG. 5 shows the path of the amplification reaction through 6 cycles. The table at the bottom summarizes the various products and their relative numbers expected for each cycle.
Figure 8:
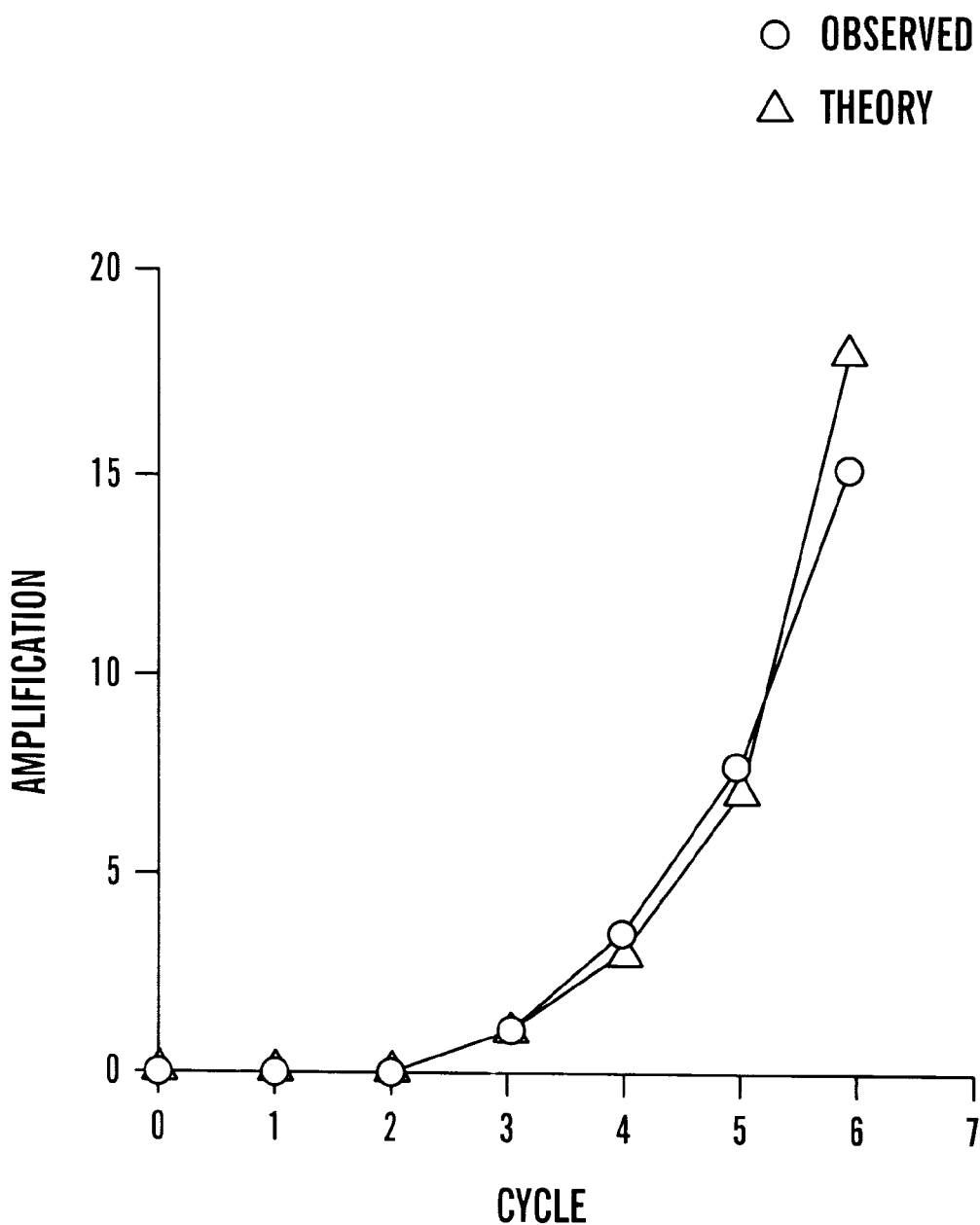
FIG. 8 is a plot of the intensities of the 1 kb band in the amplification reaction of FIG. 6 (circles). The triangles show the theoretical intensity of the 1 kb band expected from the scheme shown in FIG. 5. An intensity value of 1 was designated from the intensity of the area in the 1 kb region of the third cycle in the scan of an autoradiogram of a PCR reaction using $A.$ $aecolicus$ SSB and $\alpha\tau\delta\delta'\chi\Psi$ plus $\beta$ (similar to FIG. 7).

As discussed in Example 4 and illustrated in FIG. 5, the 1 kb PCR duplex product should not be produced in cycles 1 and 2 and, thus, is not expected to be visualized in the native gel in cycles 1 and 2. However, the 1 kb duplex should be produced in cycle 3 and produced exponentially thereafter. Indeed, examination of FIGS. 6 and 7 show no detectable 1 kb duplex produced in cycles 1 and 2 but do show the 1 kb duplex in cycles 3 through 6. Quantification of the 1 kb duplex produced in a PCR reaction using ατδδ'χΨ and Aquifex aeolicus SSB was performed by densitometric analysis of an autoradiogram of a native agarose gel. A plot of the intensity of the 1 kb band, shown in FIG. 8 (circles), shows that the product accumulates in the expected exponential fashion. The theoretical curve for the amplification path of FIG. 5 is shown for comparison (triangles). The observed result is close to the theoretical result. Further evidence that the amplification pathway proceeds as expected (i.e. as in FIG. 5) is the presence of the circular duplex and ssDNA are expected to migrate between the 1 kb duplex and the circular duplex form. Further evidence that amplification has proceeded according to the scheme of FIG. 5 are the products that arise upon omission of primer 2. Reaction without primer 2 yields no 1 kb products but does yield the circular duplex. Omission of primer 1 gives no product at all, again the expected result for the reaction path of FIG. 5.

Example 7
Formation of αε$^{mut}$τδδ'χΨ

The exonuclease activity of F requires acidic residues, D1 2 and E14, at the N-terminus. Mutation of these residues to Ala results in loss of exonuclease activity (Fijalkowska, et al., "Mutants in the Exo I Motif of Escherichia coli dnaQ: Defective Proofreading and Inviability due to Error Catastrophe," Proc. Nat'l Acad. Sci. USA 93:2856–61 (1996), which is hereby incorporated by reference). To make an ε mutant (Fmut) lacking exonuclease activity, the two acidic residues were mutated to Ala by PCR in which the upstream primer sequence encoded Ala at these two positions. The resulting ε mutant gene was cloned downstream of a T7 promotor in a Pet vector, and the recombinant plasmid was transformed into an E. coli strain containing a gene encoding the T7 RNA polymerase under control of the IPTG inducible lactose promotor. Cells were grown, induced using IPTG and the resulting ε mutant (ε$^{mut}$) was purified as described in Scheuermann et al., "A Separate Editing Exonuclease for DNA Replication: the c Subunit of Escherichia coli DNA Polymerase III Holoenzyme," Proc. Natl. Acad. Sci. USA 81:7747–7751 (1985), which is hereby incorporated by reference. The ε mut was then reconstituted into a αε$^{mut}$τδδ'χΨ complex using purified α, τ, δ, δ', χ and Ψ subunits similar to the procedure described in Example 1.

Example 8
PCR Using αε$^{mut}$τδδ'χΨ

Figure 9:
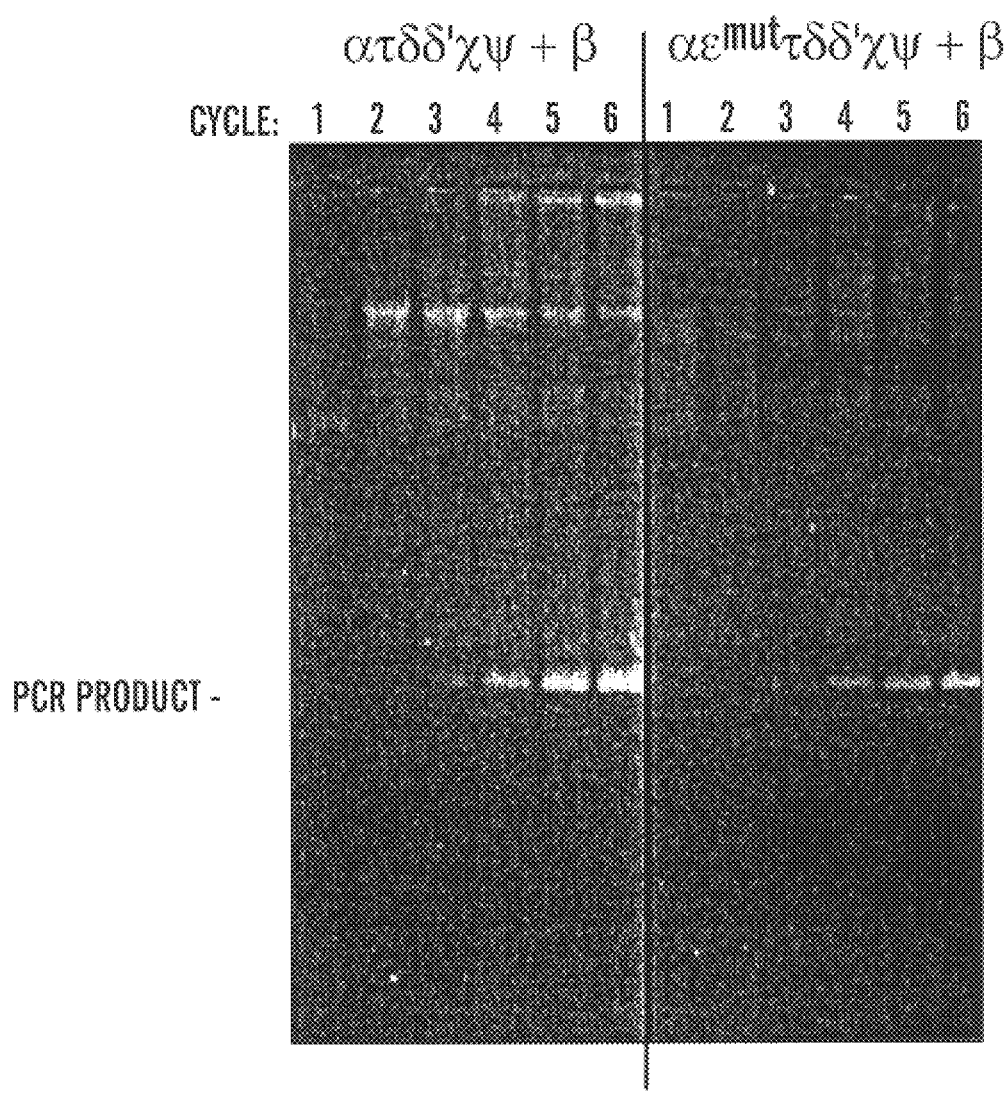
FIG. 9 is a photograph of the ethidium bromide induced fluorescence of the DNA products in a native agarose gel of two PCR reactions showing that PCR reactions using the $\alpha\epsilon^{mut}\tau\delta\delta'\chi\Psi$ complex plus $\beta$ produces a PCR product in similar fashion as the $\alpha\tau\delta\delta'\chi\Psi$ complex plus $\beta$. In each case, the $A.$ $aecolicus$ SSB was used. Cycle number is indicated at the top of the gel.

PCR reactions were performed as in Example 5 using A. aeolicus SSB (45 micrograms) and at each cycle was added 1 microgram β and 2 micrograms αε$^{mut}$τδδ'χΨ. Six cycles were performed. A photograph of the ethidium bromide induced fluorescence of the native agarose gel is shown in FIG. 9. The 1 kb duplex amplified product of the PCR reaction is produced and is visible in cycles 3–6. Hence, the physical presence of the ε subunit does not prevent amplification, consistent with the activity of ε preventing PCR product formation through exonucleolytic degradation of the primers. This result also shows that mutants of E that reduce its activity can be used for PCR.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for amplifying a nucleic acid molecule comprising:
   subjecting said nucleic acid molecule to a polymerase chain reaction process utilizing a three component DNA polymerase, wherein the three component DNA polymerase comprises a DNA polymerase component, a sliding clamp component, and a clamp loader component.

2. The method of claim 1, wherein the three component DNA polymerase has 3'–5' exonuclease activity.

3. The method of claim 2, wherein the three component DNA polymerase is a Pfu/DEEPVENT, Tli/VENT, Tth, Tma, or Tne(exo+) DNA polymerase.

4. The method of claim 1, wherein the three component DNA polymerase is isolated from a mesophilic or thermophilic organism.

5. The method of claim 4, wherein the mesophilic organism is a mesophilic bacterial cell.

6. The method of claim 5, wherein the mesophilic bacterial cell selected from the group consisting of an *Escherichia coli* a Bacillus species cell, a Salmonella species cell, a Streptococcus species cell, and a Staphylococcus species cell.

7. The method of claim 6, wherein the mesophilic bacterial cell is an *Escherichia coli* cell.

8. The method of claim 7, wherein the three component polymerase has a core Pol III comprising $\alpha$ and $\theta$ subunits.

9. The method of claim 7, wherein the three component DNA polymerase has a core Pol III comprising $\alpha$ and $\epsilon$ subunits.

10. The method of claim 7, wherein the three component DNA polymerase has a $\gamma$ complex comprising $\delta$, $\delta'$, $\chi$, and $\Psi$ subunits.

11. The method of claim 4, wherein said organism is a mammal.

12. A method for dideoxy sequencing a nucleic acid molecule comprising:
    subjecting said nucleic acid molecule to a nucleic acid sequencing process with a three component DNA polymerase, wherein the three component DNA polymerase comprises a DNA polymerase component, a sliding clamp component, and a clamp loader component.

13. The method of claim 12, wherein the three component DNA polymerase has 3'–5' exonuclease activity.

14. The method of claim 13, wherein the three component DNA polymerase is a Pfu/DEEPVENT, TliVENT, Tth, Tma, or Tne(3'exo+) DNA polymerase.

15. The method of claim 12, wherein the three component DNA polymerase is isolated from a mesophilic or thermophilic organism.

16. The method of claim 15, wherein the mesophilic organism is a mesophilic bacterial cell.

17. The method of claim 16, wherein said mesophilic bacterial cell is selected from the group consisting of an *Escherichia coli* cell, a Bacillus species cell, a Salmonella species cell, a Streptococcus species cell, and a Staphylococcus species cell.

18. The method of claim 17, wherein the mesophilic bacterial cell is an *Escherichia coli* cell.

19. The method of claim 18, wherein the three component DNA polymerase has a core Pol III comprising $\alpha$ and $\theta$ subunits.

20. The method of claim 18, wherein the three component DNA polymerase has a core Pol III comprising $\alpha$ and $\epsilon$ subunits.

21. The method of claim 18, wherein the three component DNA polymerase has a $\gamma$ complex comprising $\delta$, $\delta'$, $\chi$, and $\Psi$ subunits.

22. The method of claim 15, wherein said organism is an animal.

23. The method of claim 22, wherein said animal is a mammal.

24. A kit for amplifying a nucleic acid molecule comprising a three component DNA polymerase comprising a DNA polymerase component, a sliding clamp component, and a clamp loader component and at least one deoxynucleoside triphosphate.

25. The kit of claim 24, wherein the three component DNA polymerase is isolated from a mesophilic or thermophilic organism.

26. The kit of claim 25, wherein said mesophilic organism is a mesophilic bacterial cell.

27. The kit of claim 26, wherein the mesophilic bacterial cell is an *Escherichia coli* cell.

28. The kit of claim 27, wherein the three component DNA polymerase has a core Pol III comprising α and θ subunits.

29. The kit of claim 27, wherein the three component DNA polymerase has a core Pol III comprising α and ε subuits.

30. The kit of claim 27, wherein the three component DNA polymerase has γ complex comprising δ, δ', χ, and Ψ subunits.

31. The kit of claim 24, wherein the three component DNA polymerase has 3'–5' exonuclease activity.

32. The kit of claim 31, wherein the three component DNA polymerase is a Pfu/DEEPVENT, Tli/VENT, Tth, Tma, or Tne(3'exo+) DNA polymerase.

33. A kit for sequencing a nucleic acid molecule comprising a carrier means having in close confinement therein two or more container means, wherein a first container means contains a three component DNA polymerase comprising a DNA polymerase component, a sliding clamp component, and a clamp loader component and a second container means contains at least one dideoxynucleoside triphosphate.

34. The kit of claim 33, wherein the three component DNA polymerase is substantially reduced in 3'–5' exonuclease activity.

35. The kit of claim 33, wherein the three component DNA polymerase is isolated from a mesophilic or thermophilic organism.

36. The kit of claim 35, wherein said mesophilic organism is a mesophilic bacterial cell.

37. The kit of claim 36, wherein the mesophilic bacterial cell is an *Escherichia coli* cell.

38. The kit of claim 33, wherein the three component DNA polymerase has a core Pol III comprising α and θ subunits.

39. The kit of claim 33, wherein the three component DNA polymerase has a core Pol III comprising α and ε subunits.

40. The kit of claim 33, wherein the three component DNA polymerase has a γ complex comprising δ, δ', χ, and Ψ subunits.

41. The kit of claim 33 further comprising a DNA polymerase having 3'–5' exonuclease activity.

42. The kit of claim 41, wherein said DNA polymerase having 3'–5' exonuclease activity is a Pfu/DEEPVENT, Tli/VENT, Tth, Tma, or Tne(3'exo+) DNA polymerase.

* * * * *

UNITED STATES PATENT AND TRADEMARK OFFICE
CERTIFICATE OF CORRECTION

PATENT NO.    : 6,555,349 B1
DATED         : April 29, 2003
INVENTOR(S)   : Michael E. O'Donnell It is certified that error appears in the above-identified patent and that said Letters Patent is hereby corrected as shown below:

Title page,
Item [63], Releted U.S. Application Data, "abandoned, application No. 09/325,067, which is" should be deleted and replaced with -- abandoned. This application is also --

Signed and Sealed this

Eighteenth Day of January, 2005

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,555,349 B1 |
| APPLICATION NO. | : 09/325067 |
| DATED | : April 29, 2003 |
| INVENTOR(S) | : Michael E. O'Donnell |

It is certified that error appears in the above-identified patent and that said Letters Patent is hereby corrected as shown below:

Col. 1 at lines 19-21, delete "This invention was made based on funding under National Institutes of Health Grant No. GM38839. The United States Government may have certain rights." and insert --This invention was made with government support under grant GM38839 awarded by National Institutes of Health. The government has certain rights in the invention-- in its place.

Signed and Sealed this

Twenty-first Day of April, 2009

JOHN DOLL
*Acting Director of the United States Patent and Trademark Office*

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
gcttttgcgg gatcgtcacc                                                20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
cgatatttga agtctttcgg                                                20